(12) United States Patent
Dimitrov et al.

(10) Patent No.: US 11,236,171 B2
(45) Date of Patent: Feb. 1, 2022

(54) HUMAN MONOCLONAL ANTIBODIES SPECIFIC FOR FLT3 AND USES THEREOF

(71) Applicant: The U.S.A., as represented by the Secretary, Department of Health and Human Services, Bethesda, MD (US)

(72) Inventors: Dimiter S. Dimitrov, Frederick, MD (US); Weizao Chen, Frederick, MD (US); Terry J. Fry, Aurora, CO (US); Christopher Chien, Falls Church, VA (US); Haiying Qin, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 85 days.

(21) Appl. No.: 16/471,485

(22) PCT Filed: Dec. 21, 2017

(86) PCT No.: PCT/US2017/067974
§ 371 (c)(1),
(2) Date: Jun. 19, 2019

(87) PCT Pub. No.: WO2018/119279
PCT Pub. Date: Jun. 28, 2018

(65) Prior Publication Data
US 2019/0352408 A1    Nov. 21, 2019

Related U.S. Application Data

(60) Provisional application No. 62/437,547, filed on Dec. 21, 2016.

(51) Int. Cl.
*C07K 16/28* (2006.01)
*A61K 39/395* (2006.01)
*G01N 33/53* (2006.01)
*A61K 47/69* (2017.01)
*A61K 47/68* (2017.01)
*A61P 35/02* (2006.01)
*A61P 35/04* (2006.01)
*A61P 35/00* (2006.01)
*C07K 14/725* (2006.01)
*C07K 14/705* (2006.01)
*C07K 16/46* (2006.01)
*G01N 33/577* (2006.01)

(52) U.S. Cl.
CPC ...... *C07K 16/2863* (2013.01); *A61K 47/6849* (2017.08); *A61K 47/6929* (2017.08); *A61P 35/00* (2018.01); *A61P 35/02* (2018.01); *A61P 35/04* (2018.01); *C07K 14/7051* (2013.01); *C07K 14/70517* (2013.01); *C07K 14/70578* (2013.01); *C07K 16/468* (2013.01); *G01N 33/577* (2013.01); *C07K 2317/21* (2013.01); *C07K 2317/31* (2013.01); *C07K 2317/565* (2013.01); *C07K 2317/622* (2013.01); *C07K 2317/76* (2013.01); *C07K 2319/02* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,635,388 A | 6/1997 | Bennett et al. |
| 7,928,203 B2 | 4/2011 | Schenk et al. |
| 8,071,099 B2 | 12/2011 | Li et al. |
| 8,372,399 B2 | 2/2013 | Stolen |
| 9,023,996 B2 | 5/2015 | Grosse-Hovest et al. |
| 9,193,781 B2 | 11/2015 | Matthews et al. |
| 2003/0219827 A1 | 11/2003 | Comb et al. |
| 2009/0297529 A1 | 12/2009 | Li et al. |
| 2010/0093008 A1 | 4/2010 | Goss et al. |
| 2018/0002435 A1 | 1/2018 | Johnson et al. |
| 2018/0344702 A1 | 12/2018 | Rice et al. |
| 2018/0346601 A1 | 12/2018 | Dettling et al. |
| 2019/0038703 A1 | 2/2019 | Peled et al. |

FOREIGN PATENT DOCUMENTS

| | | |
|---|---|---|
| CN | 104288765 | 1/2015 |
| KR | 2016-0005664 | 1/2016 |
| WO | WO 2009/155015 | 12/2009 |
| WO | WO 2017/053889 | 3/2017 |
| WO | WO 2017/173410 | 10/2017 |
| WO | WO 2018/119279 | 6/2018 |
| WO | WO 2019/025484 | 2/2019 |

(Continued)

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Grafone et al., "An overview on the role of FLT3-tyrosine kinase receptor in acute myeloid leukemia: biology and treatment," *Oncol. Rev.*, vol. 6:e8, pp. 64-74, 2012.

(Continued)

*Primary Examiner* — Christine J Saoud
*Assistant Examiner* — Jon M Lockard
(74) *Attorney, Agent, or Firm* — Klarquist Sparkman, LLP

(57) ABSTRACT

Human monoclonal antibodies that specifically bind Fms-like tyrosine kinase 3 (FLT3) are described. Chimeric antigen receptors (CARs) and other antibody conjugates that include the FLT3-specific monoclonal antibodies are also described. Methods for the diagnosis and treatment of FLT3-associated cancer, such as acute lymphoblastic leukemia (ALL) or acute myeloid leukemia (AML), are further described.

26 Claims, 15 Drawing Sheets
Specification includes a Sequence Listing.

(56) References Cited

FOREIGN PATENT DOCUMENTS

| WO | WO 2019/034538 | 2/2019 |
|----|----------------|--------|
| WO | WO 2019/057649 | 3/2019 |

OTHER PUBLICATIONS

Hofmann et al., "Generation, selection and preclinical characterization of an Fc-optimized FLT3 antibody for the treatment of myeloid leukemia," *Leukemia*, vol. 26:1228-1237, 2012.
Jetani et al., "CAR T-cells targeting FLt3 have potent activity against FLT3⁻ITD⁺ AML and act synergistically with the FLT3-inhibitor crenolanib," *Leukemia* 32(5):1168-1179, 2018.
Kovtun et al., "A CD123-targeting antibody-drug conjugate, IMGN632, designed to eradicate AML while sparing normal bone marrow cells," *Blood Adv.*, vol. 2:848-858, 2018.
Lee et al., "T cells expressing CD19 chimeric antigen receptors for acute lymphoblastic leukaemia in children and young adults: a phase 1 dose-escalation trial," *Lancet* S0140-6736(14)61403-3, 2014.
Li et al., "Suppression of leukemia expressing wild-type or ITD-mutant FLT3 receptor by a fully human anti-FLT3 neutralizing antibody," *Blood*, vol. 104:1137-1144, 2004.
Piloto et al., "IMC-EB10, an Anti-FLT3 Monoclonal Antibody, Prolongs Survival and Reduces Nonobese Diabetic/Severe Combined Immunodeficient Engraftment of Some Acute Lymphoblastic Leukemia Cell Lines and Primary Leukemic Samples," *Cancer Res.*, vol. 66:4843-4851, 2006.
Stirewalt and Radich, "The role of FLT3 in haematopoietic malignancies," *Nat Rev Cancer* vol. 3(9):650-665, 2003.
Weisberg et al., "Inhibition of mutant FLT3 receptors in leukemia cells by the small molecule tyrosine kinase inhibitor PKC412," *Cancer Cell*, vol. 1:433-443, 2002.
Annesley et al., "The Biology and Targeting of FLT3 in Pediatric Leukemia," *Front. Oncol.*, vol. 4:1-18, 2014.
Armstrong et al., "MLL Translocations Specify a Distinct Gene Expression Profile that Distinguishes a Unique Leukemia," *Nature Genet.*, vol. 30:41-47, 2002.
Chien et al., "Preclinical Development of FLT3-Redirected Chimeric Antigen Receptor T Cell Immunotherapy for Acute Myeloid Leukemia," *Blood*, vol. 128:1072, 2016.
Durben et al., "Characterization of a Bispecific FLT3 X CD3 Antibody in an Improved, Recombinant Format for the Treatment of Leukemia," *Mol. Ther.*, vol. 23:648-655, 2015.
GenBank Accession No. BAC01562.1, deposited Jul. 26, 2016.
GenBank Accession No. BAC01763.1, deposited Jul. 26, 2016.
Levis, "FLT3 Mutations in Acute Myeloid Leukemia: What is the Best Approach in 2013?" *Hematology*, vol. 2013:220-226, 2013.
Levis and Small, "FLT3: ITDoes Matter in Leukemia," *Leukemia*, vol. 17:1738-1752, 2003.
Maude et al., "Chimeric Antigen Receptor T Cells for Sustained Remissions in Leukemia," *N. Eng. J. Med.*, vol. 371:1507-1517, 2014.
Piloto et al., "Inhibitory Anti-FLT3 Antibodies are Capable of Mediating Antibody-Dependent Cell-Mediated Cytotoxicity and Reducing Engraftment of Acute Myelogenous Leukemia Blasts in Nonobese Diabetic/Severe Combined Immunodeficient Mice," *Cancer Res.*, vol. 65:1514-1522, 2005.
Small, "Targeting FLT3 for Treatment of Leukemia," *Semin. Hematol.*, vol. 45:S17-S21, 2008.

* cited by examiner ary fragment) disclosed herein. Compositions that include an FLT3-specific monoclonal antibody or antigen-binding fragment and a pharmaceutically acceptable carrier are also provided by the present disclosure.

Also provided herein are nucleic acid molecules and vectors encoding the FLT3-specific monoclonal antibodies, CARs, immunoconjugates, multi-specific antibodies and fusion proteins disclosed herein.

Methods of treating an FLT3-associated cancer in a subject, and methods of inhibiting metastasis of an FLT3-associated cancer (such as a leukemia) in a subject are also provided. In some embodiments, the methods include administering to the subject a monoclonal antibody or antigen-binding fragment disclosed herein, or administering to the subject a CAR, immunoconjugate, ADC, multi-specific antibody, antibody-nanoparticle conjugate or fusion protein comprising a monoclonal antibody (or antigen-binding fragment) disclosed herein.

Further provided herein are methods of detecting expression of FLT3 in a sample. In some embodiments, the method includes contacting the sample with a monoclonal antibody or antigen-binding fragment disclosed herein, and detecting binding of the antibody to the sample.

The foregoing and other objects, features, and advantages of the invention will become more apparent from the following detailed description, which proceeds with reference to the accompanying figures.

SEQUENCE LISTING

```
<160> NUMBER OF SEQ ID NOS: 20

<210> SEQ ID NO 1
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Asn Leu Ala Pro Trp Ala Ala Tyr Trp Gly Gln Gly Thr Leu Val
            100                 105                 110

Thr Val Ser Ser
        115

<210> SEQ ID NO 2
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 2

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gln Gly Thr Lys Leu Glu Ile Lys
            100                 105                 110

<210> SEQ ID NO 3
<211> LENGTH: 729
<212> TYPE: DNA
<213> ORGANISM: Artificial Sequence
<220> FEATURE:
<223> OTHER INFORMATION: Synthetic polynucleotide

<400> SEQUENCE: 3
gaggtgcagc tggtggagtc tgggggaggc ttggtccagc ctggggggtc cctgagactc      60
tcctgtgcag cctctggatt caccttcagt agctatggca tgcactgggt ccgccaggct     120
ccaggcaagg ggctggagtg ggtggcagtt atatcatatg acggaagtaa taaatactat     180
gcagactccg tgaagggccg attcaccatc tccagagaca attccaagaa cacgctgtat     240
ctgcagatga acagcctgag agctgaggac acggctgtgt attactgtgc gaacctcgcc     300
ccgtgggctg cctactgggg ccagggaacc ctggtcaccg tctcctcagg tgaggcggt      360 tcaggcggag gtggctctgg cggtggcgga tcggaaattg tgctgactca gtctccactc     420
tccctgcccg tcacccctgg agagccggcc tccatctcct gcaggtctag tcagagcctc     480
ctgcatagta atggatacaa ctatttggat tggtacctgc agaagccagg gcagtctcca     540
cagctcctga tctatttggg ttctaatcgg gcctccgggg tccctgacag gttcagtggc     600
agtggatcag gcacagattt tacactgaaa atcagcagag tggaggctga ggatgttggg     660
gtctattact gcatgcaagc tctacaaact cctcacactt ttggccaggg gaccaaactg     720
gagatcaaa                                                             729

```
<210> SEQ ID NO 4
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Leu Ala Pro Trp Ala Ala Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Ile Val Leu Thr Gln Ser Pro Leu Ser Leu Pro Val
    130                 135                 140

Thr Pro Gly Glu Pro Ala Ser Ile Ser Cys Arg Ser Ser Gln Ser Leu
145                 150                 155                 160

Leu His Ser Asn Gly Tyr Asn Tyr Leu Asp Trp Tyr Leu Gln Lys Pro
                165                 170                 175

Gly Gln Ser Pro Gln Leu Leu Ile Tyr Leu Gly Ser Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Met Gln Ala Leu Gln Thr Pro His Thr Phe Gly Gln Gly Thr Lys Leu
225                 230                 235                 240

Glu Ile Lys

<210> SEQ ID NO 5
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 5

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Leu Ala Pro Trp Ala Ala Tyr Trp Gly Gln Gly Thr Leu Val
            100                 105                 110

Thr Val Ser Ser
        115

<210> SEQ ID NO 6
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 6

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 7
<211> LENGTH: 729
<212> TYPE: DNA
<213> ORGANISM: Artificial Sequence
<220> FEATURE:
<223> OTHER INFORMATION: Synthetic polynucleotide

<400> SEQUENCE: 7
gaggtgcagc tggtggagtc tgggggaggc gtggtccagc ctggggggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaacctcgcc     300
ccgtgggctg cctactgggg ccagggaacc ctggtcaccg tctcctcagg tggaggcggt     360
tcaggcggag gtggctctgg cggtggcgga tcggatgttg tgatgactca gtctccactc     420
tccctgcccg tcacccctgg agagccggcc tccatctcct gcaggtctag tcagagcctc     480
ctgcatagta atggatacaa ctatttggat tggtacctgc agaagccagg gcagtctcca     540
cagctcctga tctatttggg ttctaatcgg gcctccgggg tccctgacag gttcagtggc     600
agtggatcag gcacagattt tacactgaaa atcagcagag tggaggctga ggatgttggg     660
gtttattact gcatgcaagc tctacaaact cctctcactt tcggcggagg gaccaaggtg     720
gagatcaaa                                                            729

```
<210> SEQ ID NO 8
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 8
```

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Leu Ala Pro Trp Ala Ala Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Val Val Met Thr Gln Ser Pro Leu Ser Leu Pro Val
    130                 135                 140

Thr Pro Gly Glu Pro Ala Ser Ile Ser Cys Arg Ser Ser Gln Ser Leu
145                 150                 155                 160

Leu His Ser Asn Gly Tyr Asn Tyr Leu Asp Trp Tyr Leu Gln Lys Pro
                165                 170                 175

Gly Gln Ser Pro Gln Leu Leu Ile Tyr Leu Gly Ser Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Met Gln Ala Leu Gln Thr Pro Leu Thr Phe Gly Gly Gly Thr Lys Val
225                 230                 235                 240

Glu Ile Lys

```
<210> SEQ ID NO 9
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 9
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Ser Trp Val Arg Gln Ser Pro Gly Lys Gly Leu Glu
        35                  40                  45

Trp Ile Gly Glu Ile Tyr Gln Ser Gly Asn Thr Asn Tyr Asn Pro Ser
    50                  55                  60

Leu Lys Ser Arg Val Thr Ile Ser Val Asp Lys Pro Lys Asn Gln Leu
65                  70                  75                  80

Ser Leu Lys Leu Gly Ser Val Thr Ala Ala Asp Thr Ala Val Tyr Tyr
            85                  90                  95

Cys Ala Arg Gly Gly Ser Tyr Tyr Asp Tyr Trp Gly Gln Gly Thr Leu
            100                 105                 110

Val Thr Val Ser Ser
        115

<210> SEQ ID NO 10
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 10

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Val Leu
        35                  40                  45

Ile Tyr Asp Asn Asn Val Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
            85                  90                  95

Asn Val Gly Met Phe Gly Gly Gly Thr Gln Leu Ile Val Leu
            100                 105                 110

<210> SEQ ID NO 11
<211> LENGTH: 726
<212> TYPE: DNA
<213> ORGANISM: Artificial Sequence
<220> FEATURE:
<223> OTHER INFORMATION: Synthetic polynucleotide

<400> SEQUENCE: 11
caggtgcagc tgcaggagtc gggcccagga ctagtgaagc cttcacagac cctgtccctc      60
acctgcactg tctctggtgg ctccatcagc agtagtggtt actactggag ctgggtccgc     120
cagtccccag ggaaggggct ggagtggatt ggggaaatct atcaaagtgg gaacaccaac     180
tacaacccgt ccctcaagag tcgagtcacc atatcagtag acaagcccaa gaaccagctc     240
tccctgaagc tgggctctgt gaccgccgcg gacacggccg tatattactg tgcgagaggt     300
gggagctact acgactactg gggccaggga accctggtca ccgtctcctc aggtggaggc     360
ggttcaggcg gaggtggctc tggcggtggc ggatcgcagt ctgtcgtgac gcagccgccc     420
tcagtgtctg cggccccggg acagaaggtc accatctcct gctctggaag caactccaac     480
attggaaata attatgtatc gtggtaccag caactcccgg gaacagcccc caaagtcctc     540
atttatgaca ataatgttcg accctcaggg attcctgatc gattctctgg ctccaagtca     600
ggcacgtcag ccaccctggg catcaccgga ctccagactg ggacgaggc cgattattac      660 tgcgaaacat gggatagcag cctgaatgtt gggatgttcg gcggaggcac ccagctgatc     720
gtcctc                                                                726

<210> SEQ ID NO 12
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 12

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Ser Trp Val Arg Gln Ser Pro Gly Lys Gly Leu Glu
        35                  40                  45

Trp Ile Gly Glu Ile Tyr Gln Ser Gly Asn Thr Asn Tyr Asn Pro Ser
    50                  55                  60

Leu Lys Ser Arg Val Thr Ile Ser Val Asp Lys Pro Lys Asn Gln Leu
65                  70                  75                  80

Ser Leu Lys Leu Gly Ser Val Thr Ala Ala Asp Thr Ala Val Tyr Tyr
                85                  90                  95

Cys Ala Arg Gly Gly Ser Tyr Tyr Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Val Thr Gln Pro Pro Ser Val Ser Ala
    130                 135                 140

Ala Pro Gly Gln Lys Val Thr Ile Ser Cys Ser Gly Ser Asn Ser Asn
145                 150                 155                 160

Ile Gly Asn Asn Tyr Val Ser Trp Tyr Gln Gln Leu Pro Gly Thr Ala
                165                 170                 175

Pro Lys Val Leu Ile Tyr Asp Asn Asn Val Arg Pro Ser Gly Ile Pro
            180                 185                 190

Asp Arg Phe Ser Gly Ser Lys Ser Gly Thr Ser Ala Thr Leu Gly Ile
        195                 200                 205

Thr Gly Leu Gln Thr Gly Asp Glu Ala Asp Tyr Tyr Cys Glu Thr Trp
    210                 215                 220

Asp Ser Ser Leu Asn Val Gly Met Phe Gly Gly Gly Thr Gln Leu Ile
225                 230                 235                 240

Val Leu
```

<210> SEQ ID NO 13
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 13

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Val Gly Gly Gly Ala Phe Asp Ile Trp Gly Gln Gly Thr
            100                 105                 110

Met Val Thr Val Ser Ser
        115

<210> SEQ ID NO 14
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 14

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Ile Gly Asp Asn
            20                  25                  30

Tyr Val Ser Trp Tyr Gln Gln Val Pro Gly Thr Ala Pro Lys Leu Leu
         35                  40                  45

Ile Tyr Gly Asn Asn Lys Arg Pro Ser Gly Ile Pro Asp Arg Leu Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Asn Ser Leu
                 85                  90                  95

Gly Gly Val Phe Gly Gly Gly Thr Lys Leu Thr Val Leu
            100                 105

<210> SEQ ID NO 15
<211> LENGTH: 726
<212> TYPE: DNA
<213> ORGANISM: Artificial Sequence
<220> FEATURE:
<223> OTHER INFORMATION: Synthetic polynucleotide

<400> SEQUENCE: 15
gaggtgcagc tggtgcagtc tgggggaggc ttggtacagc ctggggggtc cctgagactc      60
tcctgtgcgg cctctggatt cacctttagc agctatgcca tgagctgggt ccgccaggct     120
ccagggaagg ggctggagtg ggtctcaggt attagttgga atagtggtag cataggctat     180
gcggactctg tgaagggccg attcaccatc tccagagaca cgccaagaa ctccctgtat      240
ctgcaaatga acagtctgag agctgaggac acggccttgt attactgtgc aaaagttggt     300
gggggtgggg cttttgatat ctggggccaa gggacaatgg tcaccgtctc ttcaggtgga     360
ggcggttcag gcggaggtgg ctctggcggt ggcggatcgc agtctgtgct gacgcagccg     420
ccctcagtgt ctgcggcccc aggacagaag gtcaccatct cctgctctgg aagcagctcc     480
agcattgggg ataattatgt atcctggtac cagcaggttc ccggaacagc ccccaaactc     540
ctcatttatg gcaataataa gcgaccctca gggattcctg accgactctc tggctccaag     600
tctggcacgt cagccaccct gggcatcacc ggactccaga ctgggacga ggccgattat      660
tactgcggaa catgggataa cagcctgggg ggggtgttcg gcggagggac caagctgacc     720
gtcctc                                                                726
```

<210> SEQ ID NO 16
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 16

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Gly Gly Gly Ala Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Ala Ala Pro Gly Gln Lys Val Thr Ile Ser Cys Ser Gly Ser Ser Ser
145                 150                 155                 160

Ser Ile Gly Asp Asn Tyr Val Ser Trp Tyr Gln Gln Val Pro Gly Thr
                165                 170                 175

Ala Pro Lys Leu Leu Ile Tyr Gly Asn Asn Lys Arg Pro Ser Gly Ile
            180                 185                 190

Pro Asp Arg Leu Ser Gly Ser Lys Ser Gly Thr Ser Ala Thr Leu Gly
        195                 200                 205

Ile Thr Gly Leu Gln Thr Gly Asp Glu Ala Asp Tyr Tyr Cys Gly Thr
    210                 215                 220

Trp Asp Asn Ser Leu Gly Gly Val Phe Gly Gly Gly Thr Lys Leu Thr
225                 230                 235                 240

Val Leu
```

<210> SEQ ID NO 17
<211> LENGTH: 360
<212> TYPE: DNA
<213> ORGANISM: Artificial Sequence
<220> FEATURE:
<223> OTHER INFORMATION: Synthetic polypeptide

<400> SEQUENCE: 17

```
gaggtgcagc tggtggagtc tgggggaggc ttggtacagc ctggagggtc cctgagactc      60
tcctgtgcag cctctaggtt ctacttctct gggtatgaaa tgagctgggt ccgccaggct     120
ccagggaagg gcctggagtg ggtctcagct attagtggta gtggtggtag cacatactac     180
gcagactctg tgaagggccg attcaccatc tccagagaca attccaagaa cacgctgtat     240
ctgcaaatga acagcctgag agccgaggac acggctgtgt attactgtgc gagaggggta     300
gtgggagcta agctatactt ccagcactgg ggccagggca ccctggtcac cgtctcctca     360
```

```
<210> SEQ ID NO 18
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Tyr Phe Ser Gly Tyr
            20                  25                  30

Glu Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Val Gly Ala Lys Leu Tyr Phe Gln His Trp Gly Gln
            100                 105                 110

Gly Thr Leu Val Thr Val Ser Ser
        115                 120

<210> SEQ ID NO 19
<211> LENGTH: 506
<212> TYPE: PRT
<213> ORGANISM: Artificial Sequence
<220> FEATURE:
<223> OTHER INFORMATION: Synthetic polypeptide

<400> SEQUENCE: 19

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Glu Val Gln Leu Val Glu Ser Gly Gly
        35                  40                  45

Gly Leu Val Gln Pro Gly Gly Ser Leu Arg Leu Ser Cys Ala Ala Ser
    50                  55                  60

Gly Phe Thr Phe Ser Ser Tyr Gly Met His Trp Val Arg Gln Ala Pro
65                  70                  75                  80

Gly Lys Gly Leu Glu Trp Val Ala Val Ile Ser Tyr Asp Gly Ser Asn
                85                  90                  95

Lys Tyr Tyr Ala Asp Ser Val Lys Gly Arg Phe Thr Ile Ser Arg Asp
            100                 105                 110

Asn Ser Lys Asn Thr Leu Tyr Leu Gln Met Glu Thr Asn Ser Leu Arg
        115                 120                 125

Ala Glu Asp Thr Ala Val Tyr Tyr Cys Ala Asn Leu Ala Pro Trp Ala
    130                 135                 140

Ala Tyr Trp Gly Gln Gly Thr Leu Val Thr Val Ser Ser Gly Gly
145                 150                 155                 160

Gly Ser Gly Gly Gly Gly Ser Glu Ile Val Leu Thr Gln Ser Pro Leu
                165                 170                 175
```

Ser Leu Pro Val Thr Pro Gly Glu Pro Ala Ser Ile Ser Cys Arg Ser
            180                 185                 190

Ser Gln Ser Leu Leu His Ser Asn Gly Tyr Asn Tyr Leu Asp Trp Tyr
        195                 200                 205

Leu Gln Lys Pro Gly Gln Ser Pro Gln Leu Leu Ile Tyr Leu Gly Ser
    210                 215                 220

Asn Arg Ala Ser Gly Val Pro Asp Arg Phe Ser Gly Ser Gly Ser Gly
225                 230                 235                 240

Thr Asp Phe Thr Leu Lys Ile Ser Arg Val Glu Ala Glu Asp Val Gly
                245                 250                 255

Val Tyr Tyr Cys Met Gln Ala Leu Gln Thr Pro His Thr Phe Gly Gln
            260                 265                 270

Gly Thr Lys Leu Glu Ile Lys Thr Ser Ser Gly Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Lys Arg Gly Arg Lys Lys Leu Leu Tyr Ile Phe Lys Gln Pro Phe Met
        355                 360                 365

Arg Pro Val Gln Thr Thr Gln Glu Glu Asp Gly Cys Ser Cys Arg Phe
    370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Lys Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Asn Tyr His Leu Glu Asn Glu Val Ala Arg Leu Lys Lys Leu
1               5                   10

HUMAN MONOCLONAL ANTIBODIES SPECIFIC FOR FLT3 AND USES THEREOF

CROSS REFERENCE TO RELATED APPLICATIONS

This application is the U.S. National Stage of International Application No. PCT/US2017/067974, filed Dec. 21, 2017, published in English under PCT Article 21(2) which a claims the benefit of U.S. Provisional Application No. 62/437,547, filed Dec. 21, 2016, which is herein incorporated by reference in its entirety.

ACKNOWLEDGMENT OF GOVERNMENT SUPPORT

This invention was made with government support under project numbers ZIA BC 010701 and ZIA BC 011565, awarded by the National Institutes of Health, National Cancer Institute. The government has certain rights in the invention.

FIELD

This disclosure concerns human monoclonal antibodies that specifically bind Fms-like tyrosine kinase 3 (FLT3) and uses thereof, such as for the treatment of acute lymphoblastic leukemia (ALL) and acute myeloid leukemia (AML).

BACKGROUND

Fms-like tyrosine kinase 3 (FLT3), also known as CD135, is a cytokine receptor belonging to the class III receptor tyrosine kinase family FLT3 is expressed on the surface of many hematopoietic progenitor cells and plays an important role in hematopoietic stem/progenitor cell survival and proliferation. It is frequently overexpressed in acute lymphoblastic leukemia (ALL) and is frequently mutated in acute myeloid leukemia (AML). In patients with AML, the presence of the FLT3-internal tandem duplication (ITD) mutation is a key indicator of poor long-term prognosis. The FLT3-ITD mutation occurs in approximately 25% of patients with AML. A need exists for the development of selective and potent agents against FLT3 for the treatment of ALL and FLT3-ITD AML.

SUMMARY

Disclosed herein are five fully human FLT3-specific monoclonal antibodies isolated from phage display libraries. The disclosed antibodies, referred to herein as m1006, m1007, m1008, m1009 and m1012, bind to both soluble recombinant FLT3 and cell-surface FLT3 with high affinity. Further disclosed herein is the finding that T cells expressing an FLT3-specific chimeric antigen receptor (CAR) secrete high levels of IL-2 and IFN-γ when co-cultured with FLT3-expressing AML or ALL cells. Furthermore, T cells expressing the FLT3-specific CAR were shown to eradicate FLT3-expressing ALL and AML in animal models.

Provided herein are monoclonal antibodies that bind, such as specifically bind, FLT3. In some embodiments, the monoclonal antibodies include one or more complementarity determining region (CDR) sequences of m1006, m1007, m1008, m1009 or m1012. Also provided herein are conjugates that include a disclosed FLT3-specific monoclonal antibody or antigen-binding fragment thereof. In some examples, provided are CARs, immunoconjugates, multi-specific antibodies, antibody-drug conjugates (ADCs), antibody-nanoparticles, conjugates or fusion proteins that include a monoclonal antibody or antigen-binding frag-

BRIEF DESCRIPTION OF THE DRAWINGS

(FIG. 1A) Binding of m1006 and m1007 to soluble FLT3. (FIG. 1B) Binding of m1008 and m1009 to soluble FLT3. (FIG. 1C) Binding of m1012 to soluble FLT3.

(FIG. 2A) Binding of m1006 and m1007 to FLT3-negative CHO cells. 1=cells+anti-His-PE; 2=cells+m1006+anti-His-PE; 3=cells+m1007+anti-His-PE. (FIG. 2B) Binding of m1006 and m1007 to FLT3-positive RS4; 11 cells. 1=cells+anti-His-PE; 2=cells+m1006+anti-His-PE; 3=cells+m1007+anti-His-PE. (FIG. 2C) Binding of m1008 and m1009 to FLT3-negative 293T cells. 1=cells+anti-His-PE; 2=cells+m1006 (positive control)+anti-His-PE; 3=cells+m1008+anti-His-PE; 4=cells+negative control antibody 1+anti-His-PE; 5=cells+m1009+anti-His-PE; 6=cells+negative control antibody 2+anti-His-PE. (FIG. 2D) Binding of m1008 and m1009 to FLT3-positive RS4; 11 cells. 1=cells+anti-His-PE; 2=cells+m1006 (positive control)+anti-His-PE; 3=cells+m1008+anti-His-PE; 4=cells+negative control antibody 1+anti-His-PE; 5=cells+m1009+anti-His-PE; 6=cells+negative control antibody 2+anti-His-PE. (FIG. 2E) Binding of m1012 to FLT3-negative 293T cells. 1=cells+anti-His-PE; 2=cells+anti-FLT3-PE (positive control); 3=cells+m1012+anti-His-PE. (FIG. 2F) Binding of m1012 to FLT3-positive RS4; 11 cells. 1=cells+anti-His-PE; 2=cells+anti-FLT3-PE (positive control); 3=cells+m1012+anti-His-PE. (FIG. 2G) Binding of m1012 to FLT3/IDT mutant cell line MV-4-11. 1=cells+anti-His-PE; 2=cells+anti-FLT3-PE (positive control); 3=cells+m1012+anti-His-PE.

SEQUENCE LISTING

Figure 1A:
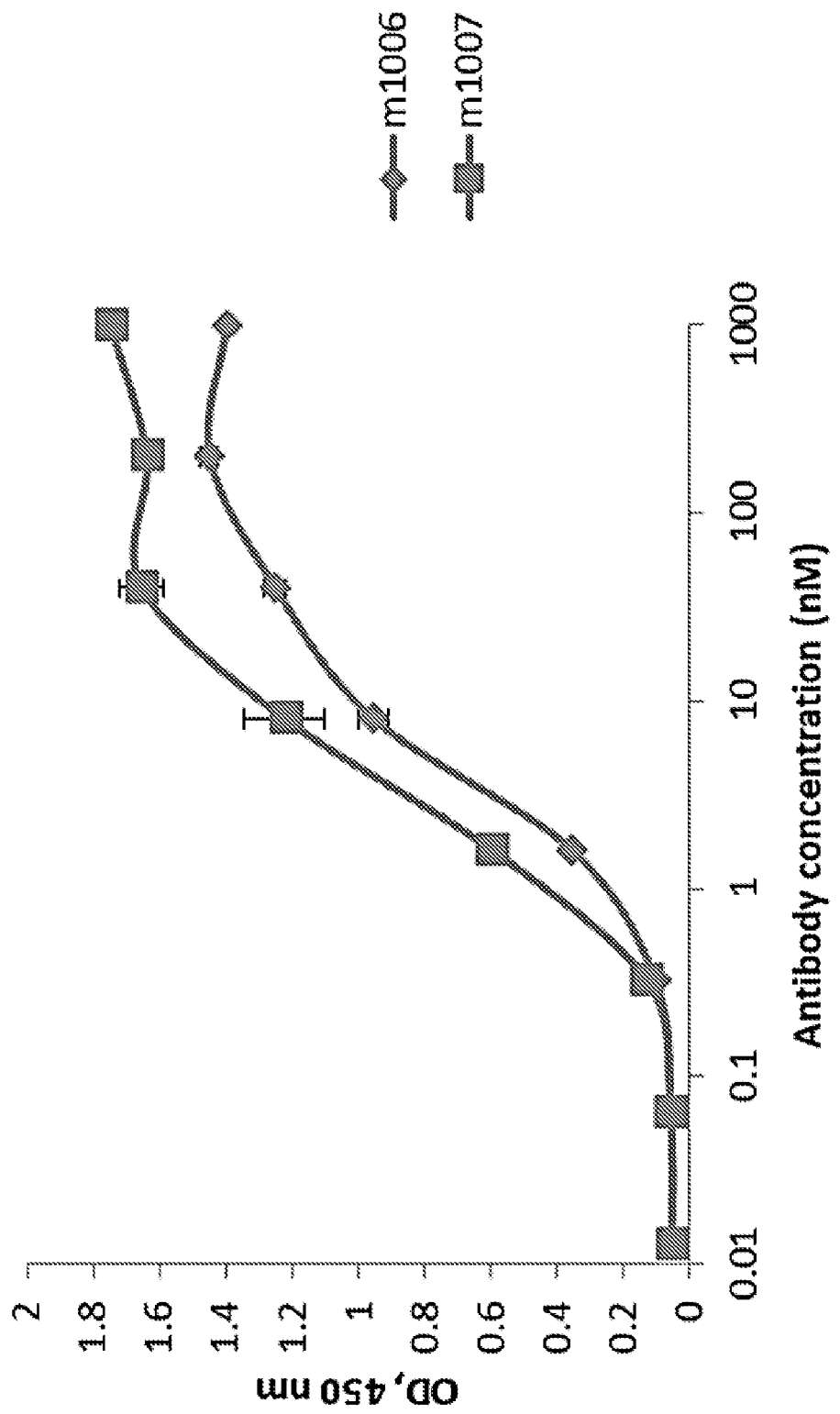
FIGS. 1A-1C are graphs showing binding of FLT3-specific antibodies to recombinant soluble FLT3 as measured by ELISA.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 10, 2019, 28.0 KB, which is incorporated by reference herein. In the accompanying sequence listing:

SEQ ID NO: 1 is the amino acid sequence of the m1006 VH domain.

SEQ ID NO: 2 is the amino acid sequence of the m1006 VL domain.

SEQ ID NO: 3 is the nucleotide sequence of the m1006 scFv.

SEQ ID NO: 4 is the amino acid sequence of the m1006 scFv.

SEQ ID NO: 5 is the amino acid sequence of the m1007 VH domain.

SEQ ID NO: 6 is the amino acid sequence of the m1007 VL domain.

SEQ ID NO: 7 is the nucleotide sequence of the m1007 scFv.

SEQ ID NO: 8 is the amino acid sequence of the m1007 scFv.

SEQ ID NO: 9 is the amino acid sequence of the m1008 VH domain.

SEQ ID NO: 10 is the amino acid sequence of the m1008 VL domain.

SEQ ID NO: 11 is the nucleotide sequence of the m1008 scFv.

SEQ ID NO: 12 is the amino acid sequence of the m1008 scFv.

SEQ ID NO: 13 is the amino acid sequence of the m1009 VH domain.

SEQ ID NO: 14 is the amino acid sequence of the m1009 VL domain.

SEQ ID NO: 15 is the nucleotide sequence of the m1009 scFv.

SEQ ID NO: 16 is the amino acid sequence of the m1009 scFv.

SEQ ID NO: 17 is the nucleotide sequence of the m1012 VH domain.

SEQ ID NO: 18 is the amino acid sequence of the m1012 VH domain.

SEQ ID NO: 19 is the amino acid sequence of a FLT3-specific chimeric antigen receptor (CAR).

SEQ ID NO: 20 is the amino acid sequence of a peptide neo-epitope (PNE).

DETAILED DESCRIPTION

I. Abbreviations

ADC antibody-drug conjugate
ALL acute lymphoblastic leukemia
AML acute myeloid leukemia
FBS fetal bovine serum
CAR chimeric antigen receptor
CDR complementarity determining region
CTL cytotoxic T lymphocyte
ELISA enzyme linked immunosorbent assay
FACS fluorescent activated cell sorting
FLT3 Fms-like tyrosine kinase 3
GFP green fluorescent protein
IFN interferon
IL interleukin
ITD internal tandem duplication
NK natural killer
PBD pyrrolobenzodiazepine
PE phycoerythrin
PE *Pseudomonas* exotoxin
scFv single chain variable fragment
TCR T cell receptor
TM transmembrane
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response.

Acute lymphoblastic leukemia (ALL): An acute form of leukemia characterized by the overproduction of lymphoblasts. ALL most frequently occurs in childhood, peaking at ages 2-5. It is the most common childhood cancer. Acute lymphoblastic leukemia is also referred to as acute lymphocytic leukemia.

Acute myeloid leukemia (AML): An aggressive form of leukemia characterized by the overproduction of myeloblasts. AML is also known as acute myeloblastic leukemia, acute myelogenous leukemia and acute nonlymphocytic leukemia (ANLL), Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light (VL) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273, 927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as FLT3) is an antibody that binds the antigen with high affinity and does not significantly bind other unrelated antigens.

Bispecific antibody: A recombinant protein that includes antigen-binding fragments of two different monoclonal antibodies, and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating AML or ALL. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds FLT3 used in combination with a radioactive or chemical compound.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate is often referred to as an "immunoconjugate." When the conjugate comprises an antibody linked to a drug (e.g., a cytotoxic agent), the conjugate is often referred to as an "antibody-drug conjugate" or "ADC." Other antibody conjugates include, for example, multispecific (such as bispecific or trispecific) antibodies and chimeric antigen receptors (CARs).

Conservative variant: "Conservative" amino acid substitutions are those substitutions that do not substantially affect or decrease the affinity of a protein, such as an antibody to FLT3. For example, a monoclonal antibody that specifically binds FLT3 can include at most about 1, at most about 2, at most about 5, and most about 10, or at most about 15 conservative substitutions and specifically bind the FLT3 polypeptide. The term "conservative variant" also includes the use of a substituted amino acid in place of an unsubstituted parent amino acid, provided that antibody specifically binds FLT3. Non-conservative substitutions are those that reduce an activity or binding to FLT3.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a FLT3 polypeptide or an antibody that binds FLT3 that includes a sequence that is degenerate as a result of the genetic code. There are 20 natural amino acids, most of which are specified by more than one codon. Therefore, all degenerate nucleotide sequences are included as long as the amino acid sequence of the FLT3 polypeptide or antibody that binds FLT3 encoded by the nucleotide sequence is unchanged.

Diagnostic: Identifying the presence or nature of a pathologic condition, such as cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as AML or ALL.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms. Therapeutic agents (or drugs) include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-FLT3 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as FLT3.

Fms-like tyrosine kinase 3 (FLT3): A class III receptor tyrosine kinase that regulates hematopoiesis. FLT3 is activated by binding of FLT3 ligand to its extracellular domain, which induces homodimer formation in the plasma membrane and autophosphorylation of FLT3. Activated FLT3 subsequently phosphorylates and activates multiple cytoplasmic effector molecules in pathways involved in apoptosis, proliferation, and differentiation of hematopoietic cells. This receptor is frequently overexpressed in acute lymphoblastic leukemia (ALL) and is frequently mutated in acute myeloid leukemia (AML). FLT3 is also known as CD135.

FLT3-associated cancer: A cancer that overexpresses FLT3 or expresses a mutant form of FLT3. Mutations in FLT3-associated cancers include, but are not limited to, internal tandem duplications in or near the juxtamembrane domain (FLT3/ITD mutations) and point mutations within the activation loop of the tyrosine kinase domain (FLT3/TKD mutations) (Levis, *Hematology Am Soc Hematol Educ Program* 2013:220-226, 2013; Levis and Small, *Leukemia* 17:1738-1752, 2003). FLT-associated cancers include, but are not limited to, ALL and AML.

FLT3-positive cancer: A cancer that overexpresses FLT3.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunoliposome: A liposome with antibodies or antibody fragments conjugated to its surface Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PBDs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_H$ of an antibody that specifically binds a FLT3 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies Specific for FLT3

Disclosed herein are five fully human FLT3-specific monoclonal antibodies isolated from phage display libraries. The disclosed antibodies, referred to herein as m1006, m1007, m1008, m1009 and m1012, bind to both soluble recombinant FLT3 and cell-surface FLT3 with high affinity. Further disclosed herein is the finding that T cells expressing a FLT-3 specific chimeric antigen receptor (CAR) secrete high levels of IL-2 and IFN-γ when co-cultured with FLT3-expressing AML or ALL cells. Furthermore, T cells expressing the FLT3-specific CAR were shown to eradicate FLT3-expressing ALL and AML in animal models.

The nucleotide and amino acid sequences of the VH and VL domains of antibodies m1006, m1007, m1008 and m1009, and the VH domain of single-domain antibody m1012, are provided below. Also shown are the nucleotide and amino acid sequences of m1006, m1007, m1008 and m1009 scFv. In the amino acid sequences below, the CDR regions according to IMGT are shown in bold underline and the residues of CDR1, CDR2 and CDR3 are indicated below each VH domain and VL domain sequence. One of skill in the art could readily determine the CDR boundaries using alternative numbering schemes, such as the Kabat or Chothia numbering schemes.

```
m1006 VH domain VH
                                                                          (SEQ ID NO: 1)
EVQLVESGGGLVQPGGSLRLSCAASGFTFSSYGMHWVRQAPGKGLEWVAVISYDGSNK

YYADSVKGRFTISRDNSKNTLYLQMNSLRAEDTAVYYCANLAPWAAYWGQGTLVTVSS

CDR1 = residues 26-33; CDR2 = residues 51-58; and CDR3 = residues 97-105 m1006 VL domain
                                                                          (SEQ ID NO: 2)
EIVLTQSPLSLPVTPGEPASISCRSSQSLLHSNGYNYLDWYLQKPGQSPQLLIYLGSNRASG

VPDRFSGSGSGTDFTLKISRVEAEDVGVYYCMQALQTPHTFGQGTKLEIK

CDR1 = residues 27-37; CDR2 = residues 55-57; and CDR3 = residues 94-102 m1006 scFv nucleotide sequence
                                                                          (SEQ ID NO: 3)
gaggtgcagctggtggagtctggggggaggcttggtccagcctggggggtccctgagactctcctgtgcagcctctggattc accttcagtagctatggcatgcactgggtccgccaggctccaggcaaggggctggagtgggtggcagttatatcatatgacg gaagtaataaatactatgcagactccgtgaagggccgattcaccatctccagagacaattccaagaacacgctgtatctgca gatgaacagcctgagagctgaggacacggctgtgtattactgtgcgaacctcgccccgtgggctgcctactggggccaggg aaccctggtcaccgtctcctcaggtggaggcggttcaggcggaggtggctctggcggtggcggatcggaaattgtgctgact cagtctccactctccctgcccgtcacccctggagagccggcctccatctcctgcaggtctagtcagagcctcctgcatagta atggatacaactataggattggtacctgcagaagccagggcagtctccacagctcctgatctatagggttctaatcgggcct ccgggggtccctgacaggacagtggcagtggatcaggcacagatatacactgaaaatcagcagagtggaggctgaggatgag gggtctattactgcatgcaagctctacaaactcctcacacttaggccaggggaccaaactggagatcaaa m1006 scFv amino acid sequence
                                                                          (SEQ ID NO: 4)
EVQLVESGGGLVQPGGSLRLSCAASGFTFSSYGMHWVRQAPGKGLEWVAVISYDGSNK

YYADSVKGRFTISRDNSKNTLYLQMNSLRAEDTAVYYCANLAPWAAYWGQGTLVTVSS

GGGGSGGGGSGGGGSEIVLTQSPLSLPVTPGEPASISCRSSQSLLHSNGYNYLDWYLQKPG

QSPQLLIYLGSNRASGVPDRFSGSGSGTDFTLKISRVEAEDVGVYYCMQALQTPHTFGQG

TKLEIK m1007 VH domain
                                                                          (SEQ ID NO: 5)
EVQLVESGGGVVQPGGSLRLSCAASGFTFSSYGMHWVRQAPGKGLEWVAVISYDGSNK

YYADSVKGRFTISRDNSKNTLYLQMNSLRAEDTAVYYCANLAPWAAYWGQGTLVTVSS

CDR1 = residues 26-33; CDR2 = residues 51-58; and CDR3 = residues 97-105
``` m1007 VL domain (SEQ ID NO: 6)

DVVMTQSPLSLPVTPGEPASISCRSSQSLLHSNGYNYLDWYLQKPGQSPQLLIYLGSNRAS

GVPDRFSGSGSGTDFTLKISRVEAEDVGVYYCMQALQTPLTFGGGTKVEIK

CDR1 = residues 27-37; CDR2 = residues 55-57; and CDR3 = residues 94-102 m1007 scFv nucleotide sequence (SEQ ID NO: 7)

gaggtgcagctggtggagtctgggggaggcgtggtccagcctggggggtccctgagactctcctgtgcagcctctggattca ccttcagtagctatggcatgcactgggtccgccaggctccaggcaaggggctggagtgggtggcagttatatcatatgatg gaagtaataaatactatgcagactccgtgaagggccgattcaccatctccagagacaattccaagaacacgctgtatctgca aatgaacagcctgagagctgaggacacggctgtgtattactgtgcgaacctcgccccgtgggctgcctactggggccaggg aaccctggtcaccgtctcctcaggtggaggcggttcaggcggaggtggctctggcggtggcggatcggatgagtgatgact cagtctccactctccctgcccgtcacccctggagagccggcctccatctcctgcaggtctagtcagagcctcctgcatagt aatggatacaactataggattggtacctgcagaagccagggcagtctccacagctcctgatctatagggttctaatcgggcc tccggggtccctgacaggttcagtggcagtggatcaggcacagattttacactgaaaatcagcagagtggaggctgaggat gttggggtttattactgcatgcaagctctacaaactcctctcactacggcggagggaccaaggtggagatcaaa m1007 scFv amino acid sequence (SEQ ID NO: 8)

EVQLVESGGGVVQPGGSLRLSCAASGFTFSSYGMHWVRQAPGKGLEWVAVISYDGSNK

YYADSVKGRFTISRDNSKNTLYLQMNSLRAEDTAVYYCANLAPWAAYWGQGTLVTVSS

GGGGSGGGGSGGGGSDVVMTQSPLSLPVTPGEPASISCRSSQSLLHSNGYNYLDWYLQKP

GQSPQLLIYLGSNRASGVPDRFSGSGSGTDFTLKISRVEAEDVGVYYCMQALQTPLTFGG

GTKVEIK m1008 VH domain (SEQ ID NO: 9)

QVQLQESGPGLVKPSQTLSLTCTVSGGSISSSGYYWSWVRQSPGKGLEWIGEIYQSGNTN

YNPSLKSRVTISVDKPKNQLSLKLGSVTAADTAVYYCARGGSYYDYWGQGTLVTVSS

CDR1 = residues 26-35; CDR2 = residues 53-59; and CDR3 = residues 98-106 m1008 VL domain (SEQ ID NO: 10)

QSVVTQPPSVSAAPGQKVTISCSGSNSNIGNNYVSWYQQLPGTAPKVLIYDNNVRPSGIPD

RFSGSKSGTSATLGITGLQTGDEADYYCETWDSSLNVGMFGGGTQLIVL

CDR1 = residues 26-33; CDR2 = residues 51-53; and CDR3 = residues 90-100 m1008 scFv nucleotide sequence (SEQ ID NO: 11)

caggtgcagctgcaggagtcgggcccaggactagtgaagcatcacagaccctgtccctcacctgcactgtctctggtggct ccatcagcagtagtggttactactggagctgggtccgccagtccccaggaaggggctggagtggattgggaaatctat caaagtgggaacaccaactacaacccgtccctcaagagtcgagtcaccatatcagtagacaagcccaagaaccagctctc cctgaagctgggctctgtgaccgccgcggacacggccgtatattactgtgcgagaggtgggagctactacgactactgggc cagggaaccctggtcaccgtctcctcaggtggaggcggttcaggcggaggtggctctggcggtggcggatcgcagtctgtc gtgacgcagccgccctcagtgtctgcggccccgggacagaaggtcaccatctcctgctctggaagcaactccaacattgga aataattatgtatcgtggtaccagcaactcccgggaacagccccaaagtcctcatttatgacaataatgacgaccctcagg gattcctgatcgattctctggctccaagtcaggcacgtcagccaccctgggcatcaccggactccagactggggacgaggc cgattattactgcgaaacatgggatagcagcctgaatgttgggatgttcggcggaggcacccagctgatcgtcctc m1008 scFv amino acid sequence
(SEQ ID NO: 12)
QVQLQESGPGLVKPSQTLSLTCTVSGGSISSSGYYWSWVRQSPGKGLEWIGEIYQSGNTN

YNPSLKSRVTISVDKPKNQLSLKLGSVTAADTAVYYCARGGSYYDYWGQGTLVTVSSGG

GGSGGGGSGGGGSQSVVTQPPSVSAAPGQKVTISCSGSNSNIGNNYVSWYQQLPGTAPKV

LIYDNNVRPSGIPDRFSGSKSGTSATLGITGLQTGDEADYYCETWDSSLNVGMFGGGTQLI

VL m1009 VH domain
(SEQ ID NO: 13)
EVQLVQSGGGLVQPGGSLRLSCAASGFTFSSYAMSWVRQAPGKGLEWVSGISWNSGSIG

YADSVKGRFTISRDNAKNSLYLQMNSLRAEDTALYYCAKVGGGGAFDIWGQGTMVTVS

S

CDR1 = residues 26-33; CDR2 = residues 51-58; and CDR3 = residues 97-107 m1009 VL domain
(SEQ ID NO: 14)
QSVLTQPPSVSAAPGQKVTISCSGSSSSIGDNYVSWYQQVPGTAPKLLIYGNNKRPSGIPDR

LSGSKSGTSATLGITGLQTGDEADYYCGTWDNSLGGVFGGGTKLTVL

CDR1 = residues 26-33; CDR2 = residues 51-53; and CDR3 = residues 90-99 m1009 scFv nucleotide sequence
(SEQ ID NO: 15)
gaggtgcagctggtgcagtctgggggaggcaggtacagcctggggggtccctgagactctcctgtgcggcctctggattca ccatagcagctatgccatgagctgggtccgccaggctccagggaaggggctggagtgggtctcaggtattagttggaatag tggtagcataggctatgcggactctgtgaagggccgattcaccatctccagagacaacgccaagaactccctgtatctgc aaatgaacagtctgagagctgaggacacggccttgtattactgtgcaaaagttggtgggggtgggcttttgatatctggg gccaagggacaatggtcaccgtctcttcaggtggaggcggttcaggcggaggtggctctggcggtggcggatcgcagtctg tgctgacgcagccgccctcagtgtctgcgccccaggacagaaggtcaccatctcctgctctggaagcagctccagcattg gggataattatgtatcctggtaccagcaggacccggaacagccccccaaactcctcatttatggcaataataagcgaccctc agggattcctgaccgactctctggctccaagtctggcacgtcagccaccctgggcatcaccggactccagactggggacgag gccgattattactgcggaacatgggataacagcctgggggggtgacggcggagggaccaagctgaccgtcctc m1009 scFv amino acid sequence
(SEQ ID NO: 16)
EVQLVQSGGGLVQPGGSLRLSCAASGFTFSSYAMSWVRQAPGKGLEWVSGISWNSGSIG

YADSVKGRFTISRDNAKNSLYLQMNSLRAEDTALYYCAKVGGGGAFDIWGQGTMVTVS

SGGGGSGGGGSGGGGSQSVLTQPPSVSAAPGQKVTISCSGSSSSIGDNYVSWYQQVPGTAP

KLLIYGNNKRPSGIPDRLSGSKSGTSATLGITGLQTGDEADYYCGTWDNSLGGVFGGGTK

LTVL m1012 VH domain nucleotide sequence
(SEQ ID NO: 17)
gaggtgcagctggtggagtctgggggaggcttggtacagcctggagggtccctgagactctcctgtgcagcctctaggttct acttctctgggtatgaaatgagctgggtccgccaggctccagggaagggcctggagtgggtctcagctattagtggtagtg gtggtagcacatactacgcagactctgtgaagggccgattcaccatctccagagacaattccaagaacacgctgtatctgca aatgaacagcctgagagccgaggacacggctgtgtattactgtgcgagaagggtagtgggagctaagctatacttccagcac tggggccagggcaccctggtcaccgtctcctca m1012 VH domain amino acid sequence (SEQ ID NO: 18)
EVQLVESGGGLVQPGGSLRLSCAASRFYFSGYEMSWVRQAPGKGLEWVSAISGSGGSTY

YADSVKGRFTISRDNSKNTLYLQMNSLRAEDTAVYYCARRVVGAKLYFQHWGQGTLVT

VSS

CDR1 = residues 26-33; CDR2 = residues 51-58; and CDR3 = residues 97-109

Provided herein are monoclonal antibodies or antigen-binding fragments that bind (such as specifically bind) FLT3, such as cell-surface FLT3 or soluble FLT3. In some embodiments, the monoclonal antibody or antigen-binding fragment includes both a VH domain and a VL domain. In other embodiments, the monoclonal antibody is a VH single-domain monoclonal antibody.

In some embodiments, the monoclonal antibody or antigen-binding fragment that binds FLT3 includes at least one CDR sequence from antibody m1006, m1007, m1008 m1009 or m1012. In some embodiments, the CDR sequences are determined using the IMGT, Kabat or Chothia numbering scheme.

In some embodiments, the FLT3-specific monoclonal antibody or antigen-binding fragment includes a VH domain and a VL domain, and the VH domain of the antibody includes one, two or all three CDR sequences of SEQ ID NO: 1, SEQ ID NO: 5, SEQ ID NO: 9 or SEQ ID NO: 13, and/or the VL domain of the antibody includes one, two or all three CDR sequences of SEQ ID NO: 2, SEQ ID NO: 6, SEQ ID NO: 10, SEQ ID NO: 14. In some examples, the VH domain comprises residues 26-33, 51-58 and 97-105 of SEQ ID NO: 1 and the VL domain comprises residues 27-37, 55-57 and 94-102 of SEQ ID NO: 2. In some examples, the VH domain comprises residues 26-33, 51-58 and 97-105 of SEQ ID NO: 5 and the VL domain comprises residues 27-37, 55-57 and 94-102 of SEQ ID NO: 6. In some examples, the VH domain comprises residues 26-35, 53-59 and 98-106 of SEQ ID NO: 9 and the VL domain comprises residues 26-33, 51-53 and 90-100 of SEQ ID NO: 10. In some examples, the VH domain comprises residues 26-33, 51-58 and 97-107 of SEQ ID NO: 13 and the VL domain comprises residues 26-33, 51-53 and 90-99 of SEQ ID NO: 14.

In particular examples, the amino acid sequence of the VH domain is at least 80%, at least 85%, at least 90%, at least 95%, at least 96%, at least 97%, at least 98% or at least 99% identical to SEQ ID NO: 1 and the amino acid sequence of the VL domain is at least 80%, at least 85%, at least 90%, at least 95%, at least 96%, at least 97%, at least 98% or at least 99% identical to SEQ ID NO: 2. In other particular examples, the amino acid sequence of the VH domain is at least 80%, at least 85%, at least 90%, at least 95%, at least 96%, at least 97%, at least 98% or at least 99% identical to SEQ ID NO: 5 and the amino acid sequence of the VL domain is at least 80%, at least 85%, at least 90%, at least 95%, at least 96%, at least 97%, at least 98% or at least 99% identical to SEQ ID NO: 6. In other particular examples, the amino acid sequence of the VH domain is at least 80%, at least 85%, at least 90%, at least 95%, at least 96%, at least 97%, at least 98% or at least 99% identical to SEQ ID NO: 9 and the amino acid sequence of the VL domain is at least 80%, at least 85%, at least 90%, at least 95%, at least 96%, at least 97%, at least 98% or at least 99% identical to SEQ ID NO: 10. In yet other particular examples, the amino acid sequence of the VH domain is at least 80%, at least 85%, at least 90%, at least 95%, at least 96%, at least 97%, at least 98% or at least 99% identical to SEQ ID NO: 13 and the amino acid sequence of the VL domain is at least 80%, at least 85%, at least 90%, at least 95%, at least 96%, at least 97%, at least 98% or at least 99% identical to SEQ ID NO: 14.

In specific non-limiting examples, the amino acid sequence of the VH domain comprises SEQ ID NO: 1 and the amino acid sequence of the VL domain comprises SEQ ID NO: 2; the amino acid sequence of the VH domain comprises SEQ ID NO: 5 and the amino acid sequence of the VL domain comprises SEQ ID NO: 6; the amino acid sequence of the VH domain comprises SEQ ID NO: 9 and the amino acid sequence of the VL domain comprises SEQ ID NO: 10; or the amino acid sequence of the VH domain comprises SEQ ID NO: 13 and the amino acid sequence of the VL domain comprises SEQ ID NO: 14.

FLT3-specific antigen-binding fragments that include both a VH domain and a VL domain can be, for example, an Fab fragment, an Fab' fragment, an F(ab)' 2 fragment, a single chain variable fragment (scFv) or a disulfide stabilized variable fragment (dsFv). In some embodiments, the antigen-binding fragment is a scFv. In some examples, the amino acid sequence of the scFv is at least 80%, at least 85%, at least 90%, at least 95%, at least 96%, at least 97%, at least 98% or at least 99% identical to SEQ ID NO: 4, SEQ ID NO: 8, SEQ ID NO: 12 or SEQ ID NO: 16. In specific examples, the amino acid sequence of the scFv comprises or consists of SEQ ID NO: 4, SEQ ID NO: 8, SEQ ID NO: 12 or SEQ ID NO: 16.

FLT3-specific monoclonal antibodies can be of any isotype, such as IgG, IgM, IgA, IgD or IgE. In some embodiments, the monoclonal antibody is an IgG.

In other embodiments, the FLT3-specific monoclonal antibody is a VH single-domain antibody that includes one, two or all three CDR sequences of SEQ ID NO: 18. In some examples, the VH domain comprises residues 26-33, 51-58 and 97-109 of SEQ ID NO: 18. In particular examples, the amino acid sequence of the VH domain is at least 80%, at least 85%, at least 90%, at least 95%, at least 96%, at least 97%, at least 98% or at least 99% identical to SEQ ID NO: 18. In one non-limiting example, the amino acid sequence of the VH domain comprises or consists of the amino acid sequence of SEQ ID NO: 18.

In some embodiments, the monoclonal antibody or antigen-binding fragment is a fully human antibody or antigen-binding fragment. In some embodiments, the monoclonal antibody or antigen-binding fragment is a chimeric or synthetic antibody or antigen-binding fragment.

Also provided herein are chimeric antigen receptors (CARs) that include a monoclonal antibody or antigen-binding fragment disclosed herein. In some embodiments, the CAR further includes a hinge region, a transmembrane domain, a costimulatory signaling moiety, a signaling domain, or any combination thereof. In some examples, the hinge region includes a CD8 hinge region; the transmembrane domain includes a CD8 transmembrane domain; the costimulatory signaling moiety includes a 4-1BB signaling moiety; and/or the signaling domain comprises a CD3ζ signaling domain. In specific examples, the CAR includes the amino acid sequence of SEQ ID NO: 19. Further provided are cells expressing an FLT3-specific CAR. In some examples, the cell is a CTL. CARs and CAR-expressing T cells are further described in section IV.

Also provided herein are immunoconjugates that include a monoclonal antibody or antigen-binding fragment disclosed herein and an effector molecule. In some embodiments, the effector molecule is a toxin, such as, but not limited to, *Pseudomonas* exotoxin or a variant thereof. In other embodiments, the effector molecule is a detectable label, such as, but not limited to, a fluorophore, an enzyme or a radioisotope. Immunoconjugates are further described in section V.

Further provided herein are antibody-drug conjugates (ADCs) that include a drug conjugated to a monoclonal antibody or antigen-binding fragment disclosed herein. In some embodiments, the drug is a small molecule, for example an anti-microtubule agent, an anti-mitotic agent and/or a cytotoxic agent. ADCs are further described in section VI.

Also provided herein are multi-specific antibodies that include a monoclonal antibody or antigen-binding fragment disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody or antigen-binding fragment disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody or antigen-binding fragment disclosed herein and a heterologous protein or peptide. In some embodiments, the heterologous protein is an Fc protein. In some examples, the Fc protein is a mouse Fc or a human Fc protein. In some embodiments, the heterologous peptide is not endogenous to humans (for example, the heterologous peptide is a peptide neo-epitope). In some embodiments, the heterologous peptide is about 8 to about 20 amino acids in length. In particular examples, the heterologous peptide is about 14 amino acids in length. In one specific, non-limiting example, the heterologous peptide comprises of consists of NYHLENEVARLKKL (SEQ ID NO: 20).

Compositions that include a pharmaceutically acceptable carrier and a monoclonal antibody or antigen-binding fragment, CAR, isolated cell, immunoconjugate, ADC, multi-specific antibody, antibody-nanoparticle conjugate, or fusion protein disclosed herein are further provided by the present disclosure.

Also provided are nucleic acid molecules encoding a monoclonal antibody or antigen-binding fragment disclosed herein. In some embodiments, the nucleic acid molecule is at least 80%, at least 85%, at least 90%, at least 95%, at least 96%, at least 97%, at least 98% or at least 99% identical to SEQ ID NO: 3, SEQ ID NO: 7, SEQ ID NO: 11, SEQ ID NO: 15 or SEQ ID NO: 17. In some examples, the nucleic acid molecule comprises or consists of SEQ ID NO: 3, SEQ ID NO: 7, SEQ ID NO: 11, SEQ ID NO: 15 or SEQ ID NO: 17. Further provided are nucleic acid molecules encoding a CAR, immunoconjugate, multi-specific antibody, or fusion protein disclosed herein. In some embodiments, the nucleic acid molecule is operably linked to a promoter. Vectors that include the nucleic acid molecules are further provided herein.

Also provided herein are methods of treating an FLT3-associated cancer in a subject, and inhibiting metastasis of an FLT3-associated cancer in a subject. In some embodiments, the method includes administering to the subject a monoclonal antibody or antigen-binding fragment disclosed herein, or administering a CAR (or CAR-expressing T cell), immunoconjugate, ADC, multi-specific antibody, antibody-nanoparticle conjugate, fusion protein, or composition comprising a monoclonal antibody or antigen-binding fragment disclosed herein. In some examples, the FLT3-associated cancer is a leukemia, such as acute lymphoblastic leukemia (ALL) or acute myeloid leukemia (AML). In specific examples, the subject with AML has the FLT3-ITD mutation.

Further provided is a method of detecting expression of FLT3 in a sample. In some embodiments, the method includes contacting the sample with a monoclonal antibody or antigen-binding fragment disclosed herein; and detecting binding of the antibody to the sample. In some examples, the monoclonal antibody or antigen-binding fragment is directly labeled. In other examples, the method further includes contacting the monoclonal antibody or antigen-binding fragment with a second antibody, and detecting the binding of the second antibody to the monoclonal antibody or antigen-binding fragment. In some examples, the sample is obtained from a subject suspected of having a FLT3-positive cancer. In some examples, the sample is a blood sample or a bone marrow biopsy.

Also provided is a method of diagnosing a subject as having an FLT3-positive cancer. In some embodiments, the method includes contacting a sample from the subject with an FLT3-specific monoclonal antibody antigen-binding fragment disclosed herein, and detecting binding of the antibody to the sample. An increase in binding of the antibody to the sample as compared to binding of the antibody to a control sample identifies the subject as having an FLT3-positive cancer. In some examples, the sample is a blood sample or a bone marrow biopsy.

IV. Chimeric Antigen Receptors (CARs)

The disclosed monoclonal antibodies can be used to produce CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In many instances, the binding moiety is an antigen binding fragment of a monoclonal antibody, such as a scFv or single-domain antibody. The spacer/hinge region typically includes sequences from IgG subclasses, such as IgG1, IgG4, IgD and CD8 domains. The transmembrane domain can be can derived from a variety of different T cell proteins, such as CD3ζ, CD4, CD8 or CD28. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

CTLs expressing CARs can be used to target a specific cell type, such as an FLT3-expressing tumor cell. Thus, the monoclonal antibodies disclosed herein can be used to engineer CTLs that express a CAR containing the FLT3-specific monoclonal antibody (for example, an scFv or a VH single-domain antibody), thereby targeting the engineered CTLs to FLT3-expressing cells, such as FLT3-expressing AML or ALL cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a FLT3-specific antibody. In some embodiments, the CAR includes the sequence set forth herein as SEQ ID NO: 19:

MALPVTALLLPLALLLHAARPDYKDDDDKGGGGSGGGGSEVQLVESGGGL

VQPGGSLRLSCAASGFTFSSYGMHWVRQAPGKGLEWVAVISYDGSNKYYA

DSVKGRFTISRDNSKNTLYLQMetNSLRAEDTAVYYCANLAPWAAYWGQG

TLVTVSSGGGGSGGGGSEIVLTQSPLSLPVTPGEPASISCRSSQSLLHSN

GYNYLDWYLQKPGQSPQLLIYLGSNRASGVPDRFSGSGSGTDFTLKISRV

EAEDVGVYYCMQALQTPHTFGQGTKLEIKTSSGTTTPAPRPPTPAPTIAS

QPLSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKFSR

SADAPAYKQGQNQLYNELNLGRREEYDVLDKRRGRDPEMGGKPRRKNPQE

GLYNELQKDKMAEAYSEIGMKGERRRGKGHDGLYQGLSTATKDTYDALHM

QALPPR

| Feature | Residues |
|---|---|
| Human CD8α signal peptide | 1-21 |
| FLAG peptide | 22-29 |
| Linker | 30-39 |
| Heavy Chain | 40-157 |
| Linker | 158-167 |
| Light Chain | 168-279 |
| CD8α transmembrane | 284-352 |
| 41BB intracellular domain | 353-395 |
| CD3ζ intracellular domain | 395-506 |

Also provided are isolated nucleic acid molecules and vectors encoding the CARs, and host cells, such as CTLs, expressing the CARs. CTLs expressing CARs comprised of a FLT3-specific monoclonal antibody can be used for the treatment of cancers that express FLT3. In some embodiments herein, the CAR is a bispecific CAR.

In some instances, it is desirable to regulate the activation and expansion of CAR-expressing T cells after they have been infused into a patient. Several strategies have been developed to module CAR-expressing T cells in vivo, including the use of antibody-based switches that mediate interactions between CAR-expressing T cells and targeted tumors cells, as described by Rodgers et al. (*Proc Natl Acad Sci USA* 113(4):E459-E468, 2016, which is incorporated herein by reference). The antibody-based switches are comprised of a tumor antigen-specific antibody that has been grafted with a peptide neo-epitope (PNE). Switchable CAR T (sCAR-T) cells are designed to specifically bind the PNE. Since the sCAR-T cells do not bind endogenous antigens, the presence of the switch is required for its activation.

Thus, provided herein are antibody-based switches that include a FLT3-specific monoclonal antibody disclosed herein fused to a heterologous peptide, such as a PNE. In some embodiments, the heterologous peptide is not endogenous to humans (for example, it is a peptide that is not found in the human proteome). In some examples, the heterologous peptide is about 8 amino acids to about 20 amino acids in length, such about 10 to about 18 amino acids in length, such as about 12 to about 16 amino acids in length, such as about 14 amino acids in length. In particular examples, the heterologous peptide is about 8, 9, 10, 11, 12, 13, 14, 15, 16, 17, 18, 19 or 20 amino acids in length. In a specific non-limiting example, the PNE comprises or consists of NYHLENEVARLKKL (SEQ ID NO: 20).

V. Immunoconjugates

The disclosed monoclonal antibodies can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}I$, $^{32}P$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH₂) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

The antibodies described herein can also be used to target any number of different diagnostic or therapeutic compounds to cells expressing the tumor or viral antigen on their surface. Thus, an antibody of the present disclosure can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

ADCs are compounds comprised of a tumor antigen-specific antibody (or antigen-binding fragment thereof) and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1)

or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-ketogalactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) FLT3. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, vinca alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663,149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of an FLT3-associated cancer alone or in combination with another therapeutic agent and/or in combination with any standard therapy for the treatment of cancer (such as surgical resection of the tumor, chemotherapy or radiation therapy).

VII. Multi-Specific Antibodies

Multi-specific antibodies are recombinant proteins comprised of antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The FLT3-specific monoclonal antibodies disclosed herein can be used to generate multi-specific (such as bispecific or trispecific) antibodies that target both FLT3 and CTLs, or target both FLT3 and NK cells, thereby providing a means to treat FLT3-expressing cancers.

Bi-specific T-cell engagers (BiTEs) are a type of bispecific monoclonal antibody that are fusions of a first single-chain variable fragment (scFv) that targets a tumor antigen and a second scFv that binds T cells, such as bind CD3 on T cells. In some embodiments herein, one of the binding moieties of the BiTE (such as one of the scFv molecules) is specific for FLT3.

Bi-specific killer cell engagers (BiKEs) are a type of bispecific monoclonal antibody that are fusions of a first scFv that targets a tumor antigen and a second scFv that binds a NK cell activating receptor, such as CD16.

Provided herein are multi-specific, such as trispecific or bispecific, monoclonal antibodies comprising a FLT3-specific monoclonal antibody. In some embodiments, the multi-specific monoclonal antibody further comprises a monoclonal antibody, or antigen-binding fragment thereof, that specifically binds a component of the T cell receptor, such as CD3. In other embodiments, the multi-specific monoclonal antibody further comprises a monoclonal antibody, or antigen-binding fragment thereof, that specifically binds a NK cell activating receptor, such as CD16, Ly49, or CD94. Also provided are isolated nucleic acid molecules and vectors encoding the multi-specific antibodies, and host cells comprising the nucleic acid molecules or vectors. Multi-specific antibodies comprising a FLT3-specific antibody can be used for the treatment of cancers that express FLT3. Thus, provided herein are methods of treating a subject with cancer by selecting a subject with a cancer that expresses FLT3, and administering to the subject a therapeutically effective amount of the FLT3-targeting multi-specific antibody.

VIII. Antibody-Nanoparticle Conjugates

The monoclonal antibodies disclosed herein can be conjugated to a variety of different types of nanoparticles to deliver cytotoxic agents or other anti-cancer agents directly to tumor cells via binding of the antibody to a tumor specific antigen (e.g. FLT3) expressed on the surface of tumor cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies, including scFv and single-domain antibodies, can be conjugated to a suitable nanoparticle according to standard methods known in the art. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31)5239-5277, 2012).

IX. Compositions and Methods of Use

Compositions are provided that include one or more of the disclosed monoclonal antibodies that bind (for example specifically bind) FLT3 in a carrier. Compositions comprising CARs (and CTLs comprising CARs), ADCs, multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, CAR, ADC, CTL, multi-specific antibody, antibody-nanoparticle conjugate, immunoliposome or immunoconjugate can be formulated for systemic or local administration. In one example, the antibody is formulated for parenteral administration, such as intravenous administration.

The compositions for administration can include a solution of the antibody, CAR, CTL, ADC, multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, CARs, ADCs, multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.*

44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, multi-specific (such as bispecific or trispecific) antibodies, antibody-nanoparticle conjugates, immunoliposomes and immunoconjugates disclosed herein can be administered to slow or inhibit the progression of an FLT3-associated cancer, or inhibit the metastasis of an FLT3-associated cancer. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses FLT3, such as a leukemia, for example ALL or AML.

Provided herein is a method of treating a FLT3-associated cancer in a subject by administering to the subject a therapeutically effective amount of a FLT3-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. Also provided herein is a method of inhibiting metastasis of a FLT3-associated cancer in a subject by administering to the subject a therapeutically effective amount of a FLT3-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. In some embodiments, the FLT3-associated cancer is a leukemia, such as ALL or AML.

A therapeutically effective amount of a FLT3-specific monoclonal antibody, CAR (e.g. a CTL expressing a CAR), ADC, multi-specific (such as bispecific or trispecific) antibody, immunoconjugate, immunoliposome or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the FLT3-specific antibodies, CARs, ADCs, immunoconjugates, multi-specific (such as bispecific or trispecific) antibodies, antibody-nanoparticle conjugates, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of a metastatic tumor. Another example of a treatment is radiotherapy, for example administration of radioactive material or energy (such as external beam therapy) to the tumor site to help eradicate the tumor or shrink it prior to surgical resection.

Therapeutic agents for the treatment of AML and/or ALL are known in the art and can be administered in combination with any of the FLT3-specific antibodies or antibody conjugates disclosed herein. In some embodiments, the subject is treated with an inhibitor of FLT3, such as lestaurtinib (CEP-701), midostaurin (PKC412), quizartinib (AC220), sorafenib (BAY-93006), sunitinib (SU11248), tandutinib (MLN518) or ASP2215 (Annesley and Brown, Front Oncol 4:263, 2014; Small, *Semin Hematol* 45(3 Suppl 2):517-S21, 2008). In some embodiments, the subject is treated with an anti-leukemic therapeutic agent, such as cytarabine, idarubicin, etoposide, methotrexate or clofarabine. In some embodiments, the patient receives a hematopoietic stem cell transplant.

B. Methods for Diagnosis and Detection

Methods are provided herein for detecting FLT3 protein in vitro or in vivo. In some cases, FLT3 expression is detected in a biological sample. The sample can be any sample, including, but not limited to, blood samples, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of determining if a subject has a FLT3-associated cancer by contacting a sample from the subject with a FLT3-specific monoclonal antibody disclosed herein; and detecting binding of the antibody to the sample. An increase in binding of the antibody to the sample as compared to binding of the antibody to a control sample identifies the subject as having a FLT3-associated cancer.

In another embodiment, provided is a method of confirming a diagnosis of a FLT3-associated cancer in a subject by contacting a sample from a subject diagnosed with a FLT3-associated cancer with a FLT3-specific monoclonal antibody disclosed herein; and detecting binding of the antibody to the sample. An increase in binding of the antibody to the sample as compared to binding of the antibody to a control sample confirms the diagnosis of a FLT3-associated cancer in the subject.

In some examples of the disclosed methods, the monoclonal antibody is directly labeled.

In other examples, the methods further include contacting a second antibody that specifically binds the monoclonal antibody with the sample; and detecting the binding of the second antibody. An increase in binding of the second antibody to the sample as compared to binding of the second antibody to a control sample detects a FLT3-associated cancer in the subject or confirms the diagnosis of a FLT3-associated cancer in the subject.

In some cases, the cancer is a leukemia. In specific non-limiting examples, the leukemia is ALL or AML.

In some examples, the control sample is a sample from a subject without cancer. In particular examples, the sample is a blood or tissue sample, such as a bone marrow biopsy.

In some embodiments of the methods of diagnosis and detection, the antibody that binds (for example specifically binds) FLT3 is directly labeled with a detectable label. In another embodiment, the antibody that binds (for example, specifically binds) FLT3 (the first antibody) is unlabeled and a second antibody or other molecule that can bind the antibody that specifically binds FLT3 is labeled. As is well known to one of skill in the art, a secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, FLT3 can be assayed in a biological sample by a competition immunoassay utilizing FLT3 protein standards labeled with a detectable substance and an unlabeled antibody that specifically binds FLT3. In this assay, the biological sample, the labeled FLT3 protein standards and the antibody that specifically bind FLT3 are combined and the amount of labeled FLT3 protein standard bound to the unlabeled antibody is determined. The amount of FLT3 in the biological sample is inversely proportional to the amount of labeled FLT3 protein standard bound to the antibody that specifically binds FLT3.

The immunoassays and methods disclosed herein can be used for a number of purposes. In one embodiment, the antibody that specifically binds may be used to detect the production of FLT3 in cells in cell culture. In another embodiment, the antibody can be used to detect the amount of FLT3 in a biological sample, such as a tissue sample, or a blood or serum sample. In some examples, the FLT3 is cell-surface FLT3. In other examples, the FLT3 protein is soluble (e.g. in a cell culture supernatant or in a body fluid sample, such as a blood or serum sample).

In one embodiment, a kit is provided for detecting FLT3 in a biological sample, such as a blood sample or tissue sample. For example, to confirm a cancer diagnosis in a subject, a biopsy can be performed to obtain a tissue sample for histological examination. Kits for detecting a polypeptide will typically comprise a monoclonal antibody that specifically binds FLT3, such as any of the monoclonal antibodies disclosed herein. In a further embodiment, the antibody is labeled (for example, with a fluorescent, radioactive, or an enzymatic label).

In one embodiment, a kit includes instructional materials disclosing means of use of an antibody that binds FLT3. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting FLT3 in a biological sample generally includes the steps of contacting the biological sample with an antibody which specifically reacts, under immunologically reactive conditions, to FLT3. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind FLT3, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Fully Human Monoclonal Antibodies Specific for FLT3

This example describes the identification and characterization of five fully human FLT3-specific monoclonal antibodies referred to as m1006, 1007, 1008, 1009 and m1012.

The human monoclonal antibodies were isolated from phage display Fab (m1006 and m1007), scFv (m1008 and m1009) and VH domain (m1012) libraries. The phage libraries were cycled through three rounds of selection with biotinylated recombinant human FLT3 and streptavidin-conjugated magnetic beads. FLT3 binders were identified by using monoclonal phage ELISA (for Fab library) or soluble expression-based monoclonal ELISA (for scFv and VH libraries) according to previously described protocols (Chen et al., *Mol Immunol* 2010, 47:912-921, 2010).

Figure 1B:
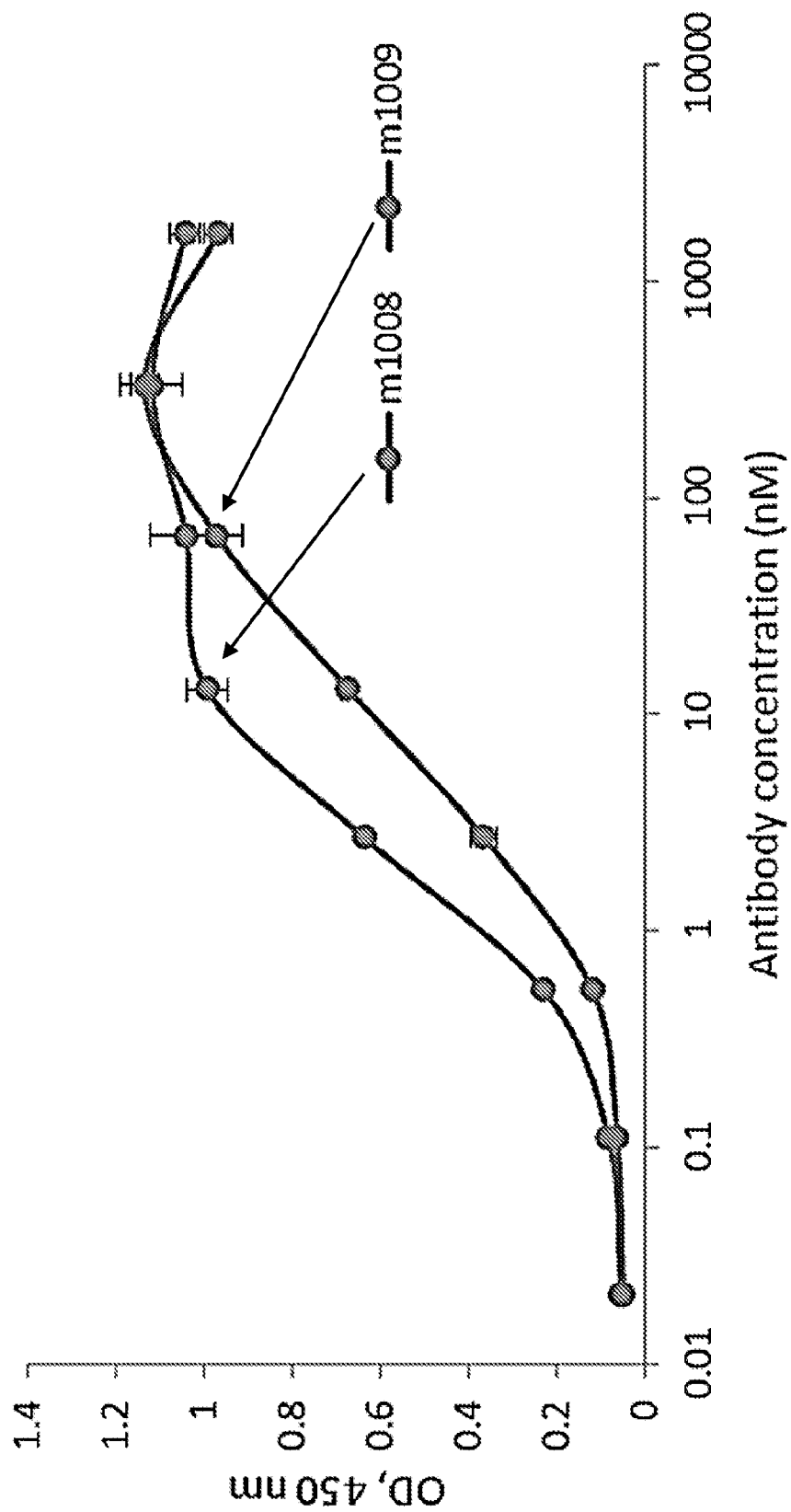
Figure 1C:
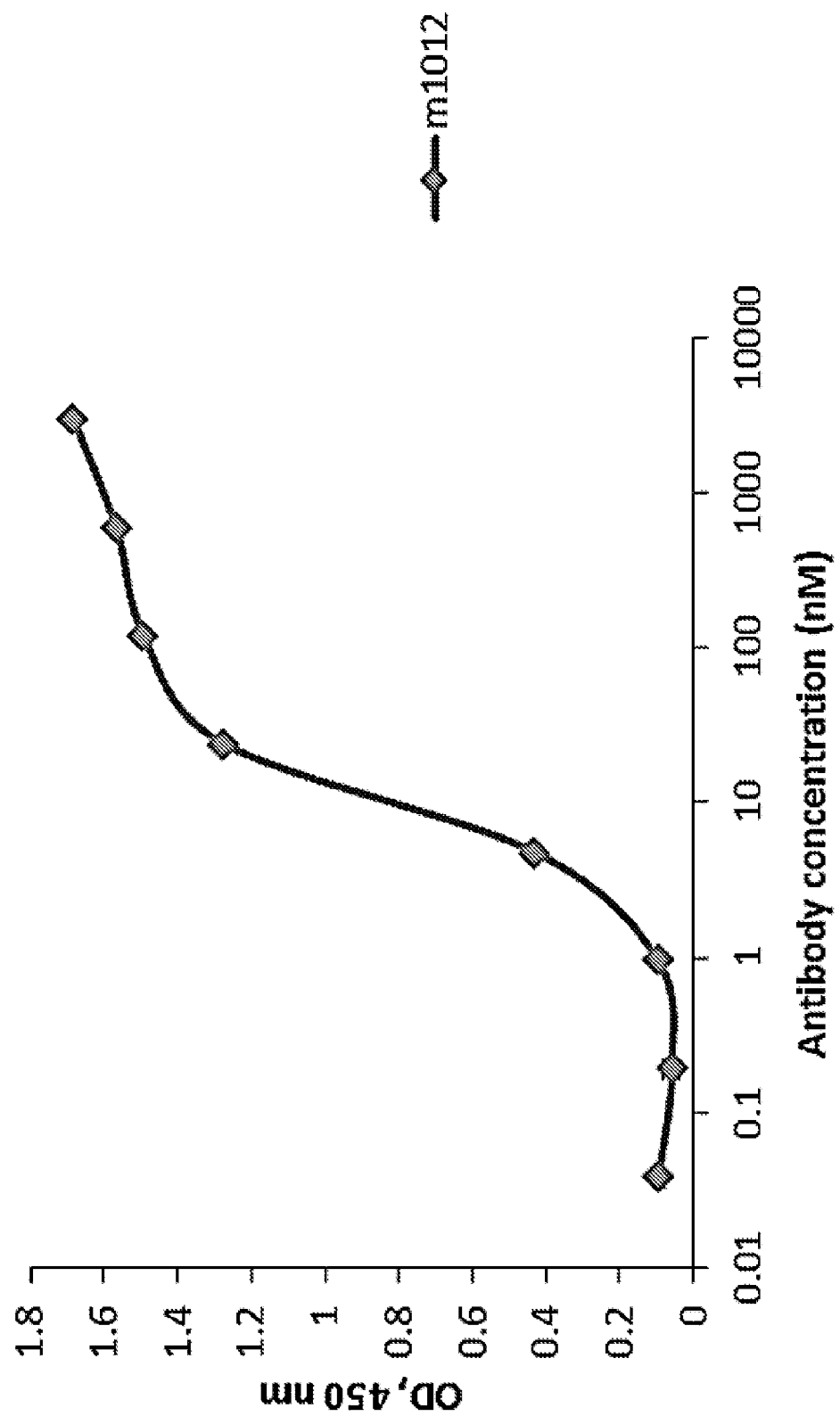
Figure 2A:
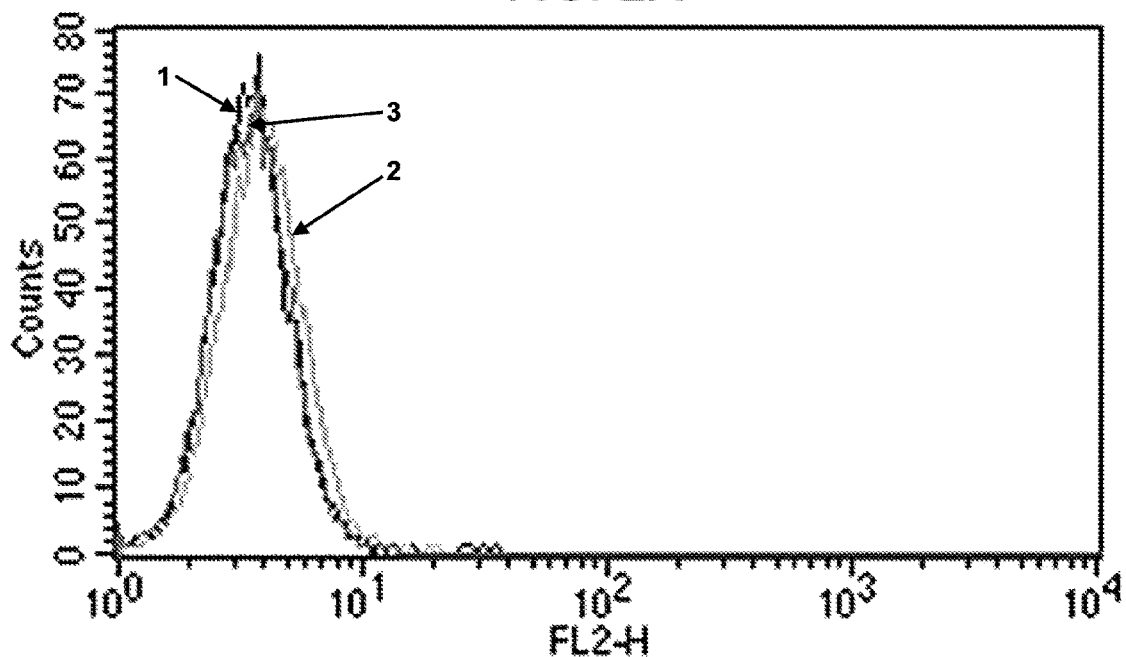
FIGS. 2A-2G are FACS plots showing binding of FLT3-specific antibodies to FLT3-positive and FLT3-negative cell lines.
Figure 2B:
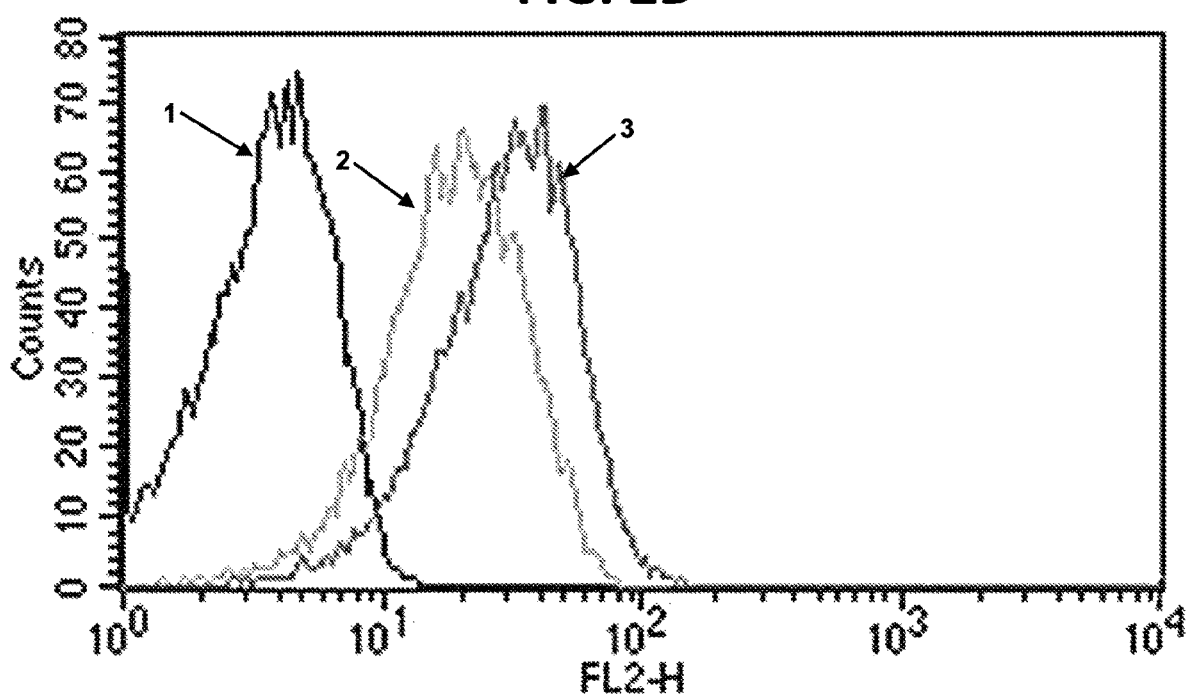
Figure 2C:
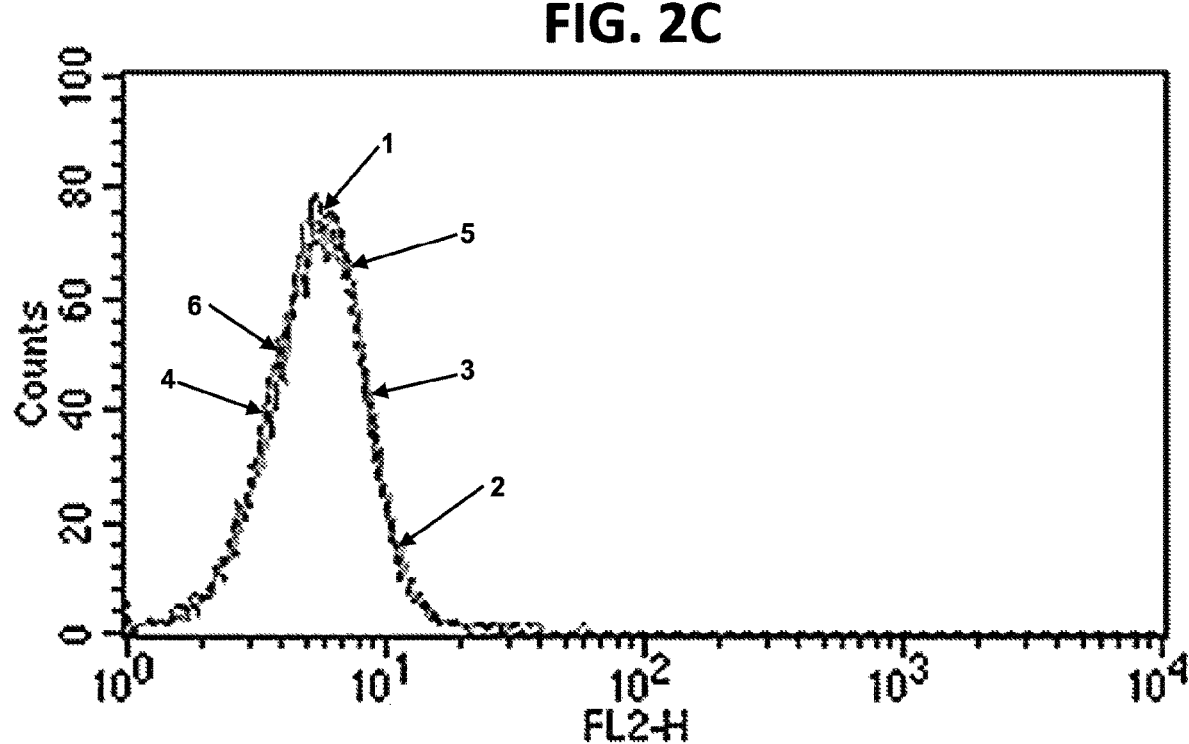
Figure 2D:
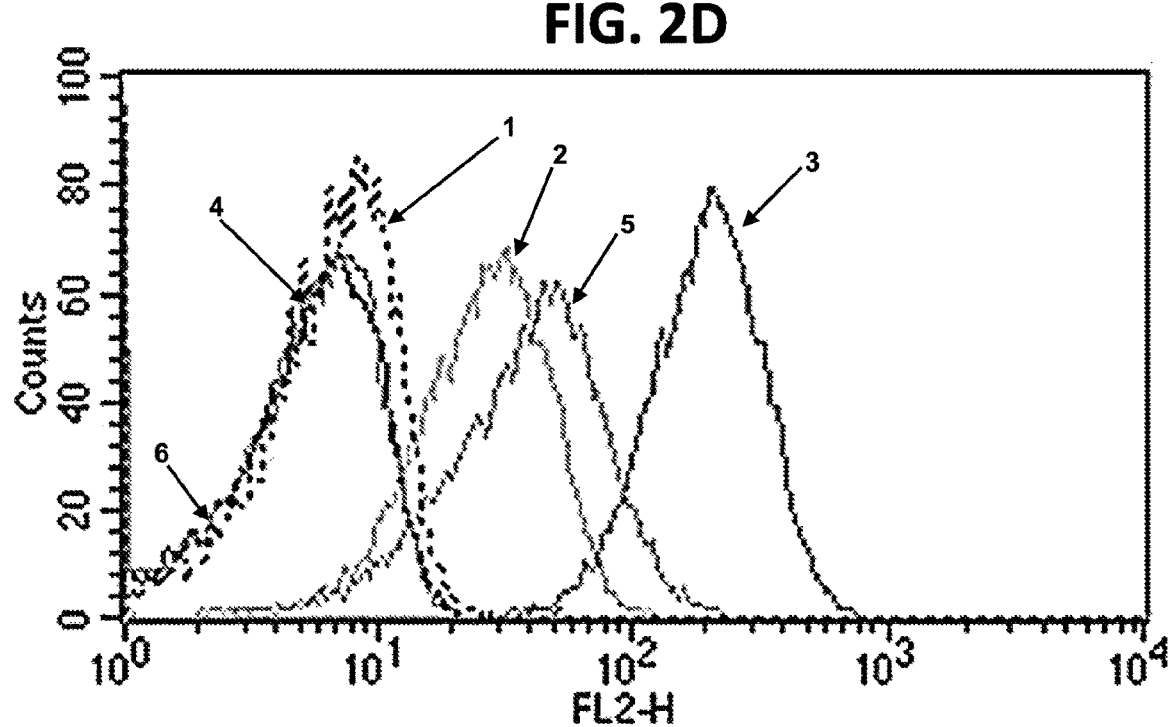
Figure 2E:
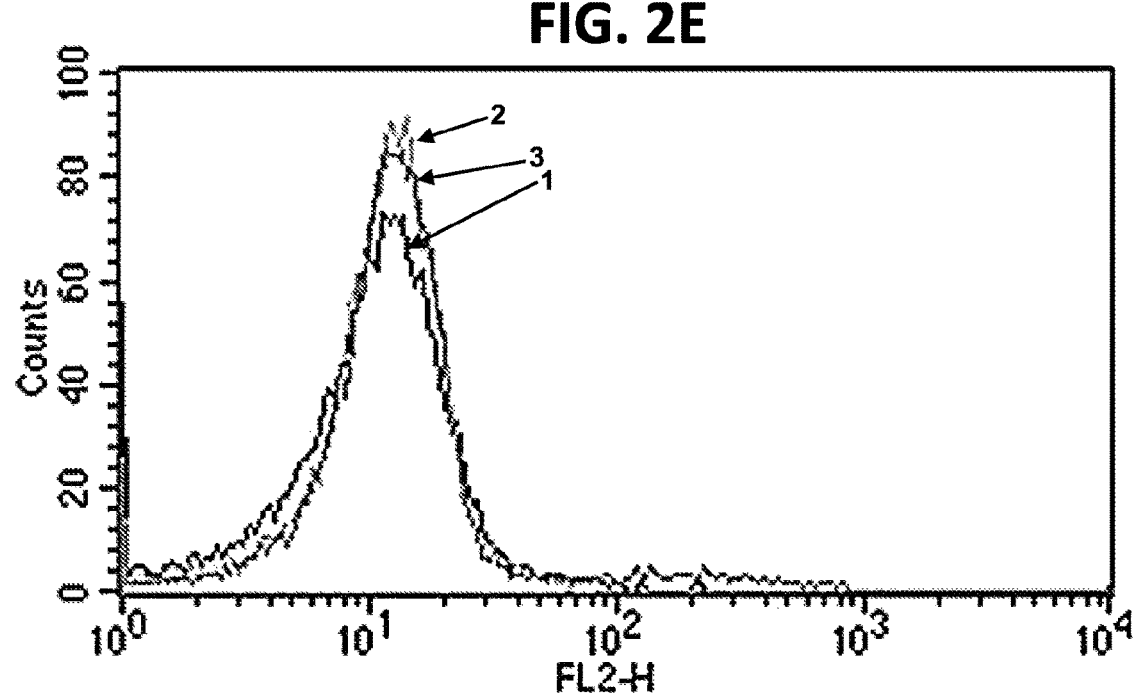
Figure 2F:
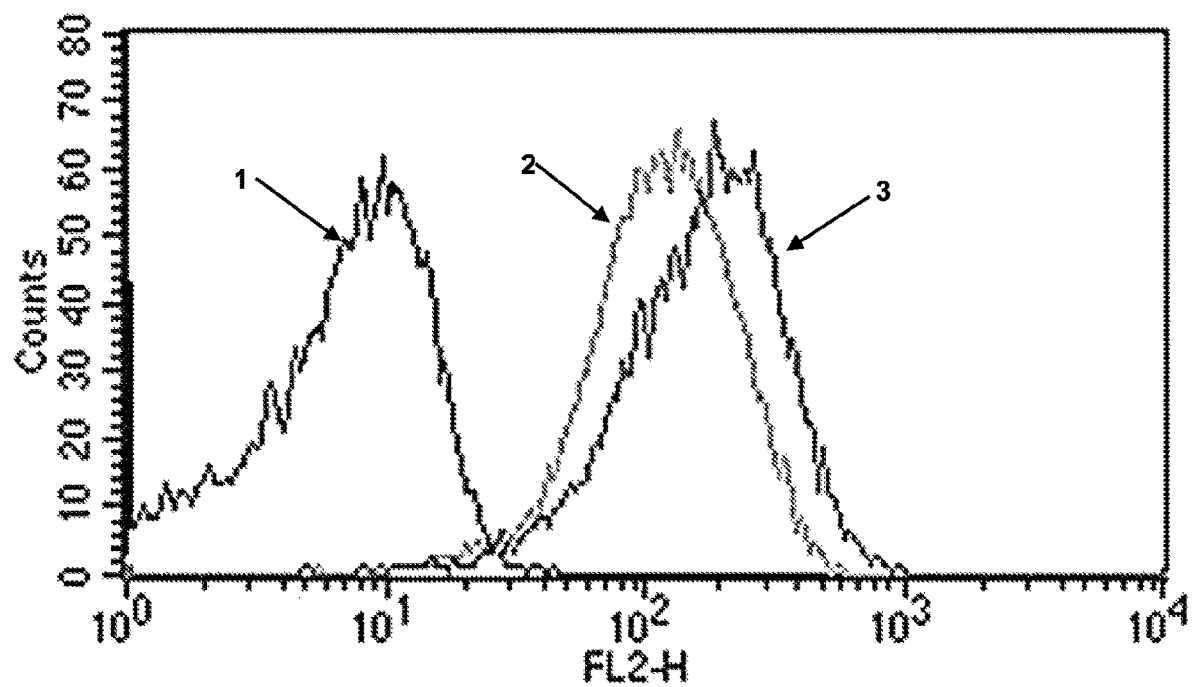
Figure 2G:
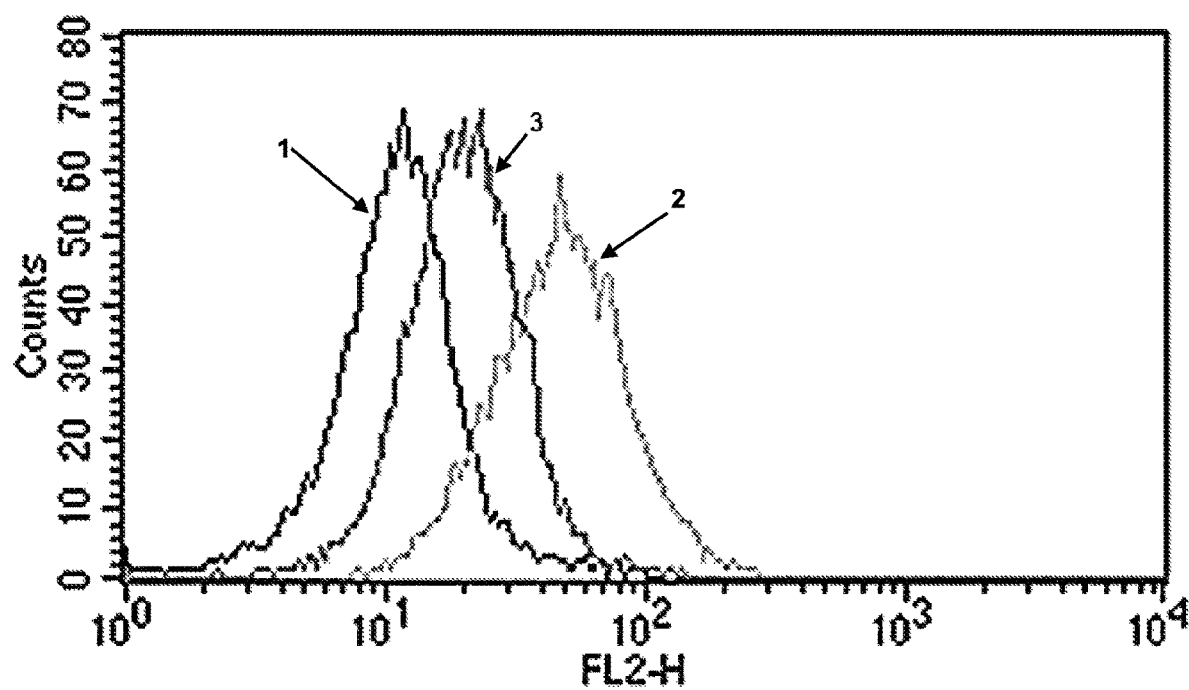

To evaluate binding affinity of the identified antibodies for FLT3, binding of m1006, 1007, 1008, 1009 and m1012 to recombinant soluble FLT3 was determined by ELISA. The results are shown in FIGS. 1A-1C. Additional experiments were performed using flow cytometry to determine whether m1006, 1007, 1008, 1009 and m1012 could bind cell-surface FLT3. None of the FLT3-specific antibodies bound to FLT-negative cells (FIGS. 2A, 2C and 2E). However, m1006, m1007, m1008, m1009 and m1012 all bound FLT3-positive RS4; 11 cells (FIGS. 2B, 2D and 2F). In addition, m1012 was shown to bind the FLT3/IDT mutant cell line MV-4-11 (FIG. 2G).

Example 2: FLT3-Specific Chimeric Antigen Receptor (CAR)

This example describes the generation of characterization of a CAR that includes the FLT3-specific m1006 scFv.

Chimeric antigen receptors (CARs) combine an antibody-based binding domain (such as a single chain fragment variable region, scFv) with T cell receptor signaling domains (for example, CD3$\zeta$ with a costimulatory domain, such as CD28 or 4-1BB). When T cells express CARs they are activated in an MHC-independent manner to kill tumor cells expressing the target to which the antibody or antibody fragment binds. CAR-expressing T cells targeting the B cell antigen CD19 have resulted in substantial response rates in patients with pre-B cell precursor acute lymphoblastic leukemia (ALL), demonstrating the potency of CAR therapy. Despite the high response rates observed in these clinical trials, there are still leukemic patient populations where standard therapies are sub-optimal. Patients with infant ALL or AML have dismal survival rates of less than 40 and 60% respectively, thus a need remains for alternative therapies. Since these groups of patients express high levels of FLT3, treatment with CAR-expressing immune cells directed at FLT3 provides a viable therapeutic option. FLT3 is frequently mutated in AML, causing activation of the pathway and is thought to be a major driver of disease. Thus, down-modulation of FLT3 is an improbable escape mechanism. Additionally, the mutations are found in the intracellular domain of the receptor so immune cells expressing FLT3 CARs will be able to target both wild type and mutant forms of FLT3 allowing for broad targeting of both infant ALL and AML.

Figure 3:
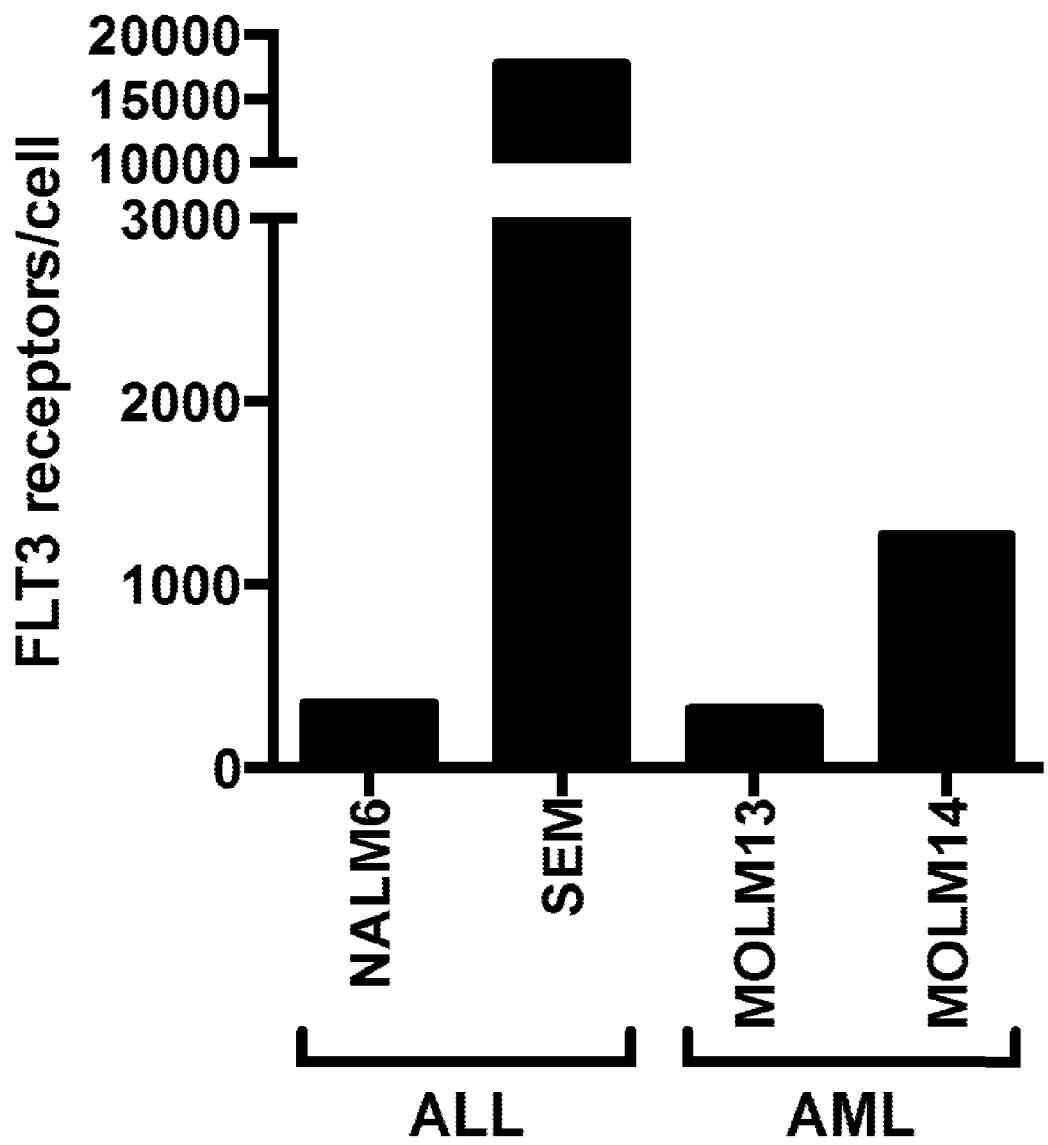
FIG. 3 is a graph showing expression of FLT3 on acute lymphoblastic and acute myeloid leukemia cells lines. The number of FLT3 receptors per cell was quantified on acute lymphoblastic leukemia cells, NALM6 (DSMZ ACC 128) and SEM (ACC 546), and on acute myeloid leukemia cells, MOLM13 (DSMZ ACC 554) and MOLM14 (DSMZ ACC 577), by flow cytometry.

The number of FLT3 molecules on the surface of several different acute lymphoblastic (NALM6 and SEM) and acute myeloid (MOLM13 and MOLM14) leukemia cell lines was evaluated. Each of the cell lines expressed FLT3, with SEM cells expressing the greater number of FLT3 molecules per cell (FIG. 3).

Figure 4:
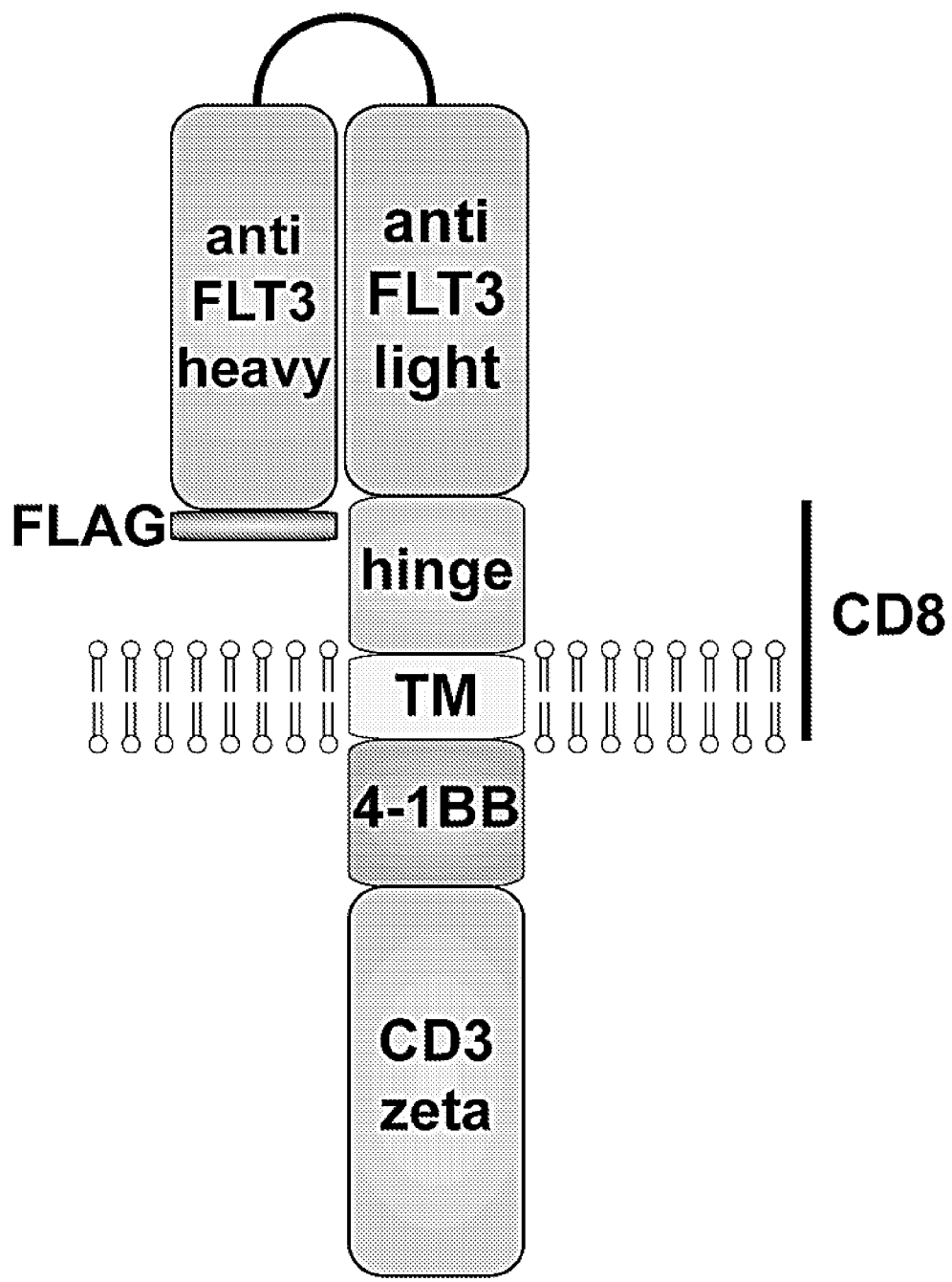
FIG. 4 is a diagram of an FLT3-specific CAR. Illustrated is a mature FLT3 CAR consisting of an FLT3-specific scFv. The scFv is fused to the CD8 hinge and transmembrane (TM) regions, 4-1BB intracellular T cell costimulatory domain, and CD3ζ intracellular T cell activation domain.

To target T cells to FLT3-expressing leukemia cells, a CAR was constructed. A diagram of the FLT3-specific CAR is shown in FIG. 4. Antibody m1006 was converted into a single chain fragment variable (scFv) and fused to the CD8 hinge and transmembrane (TM) regions, 4-1BB intracellular T cell costimulatory domain, and CD3zeta intracellular T cell activation domain. The amino acid sequence encoding the FLT3-specific scFv was converted to DNA sequence and codon optimized synthesized using GeneArt gene synthesis (ThermoFisher Scientific; Waltham, Mass.) with Kozak sequence, membrane localization leader sequence from human CD8 alpha, 5' NheI restriction site, and 3' BspEI restriction site. The FLT3-targeted scFV sequence was then subcloned from the provided GeneArt vector and moved to the third generation lentiviral plasmid pELNS-19BB$\zeta$ which contains the CD8$\alpha$ hinge and transmembrane, 4-1BB signaling domain, and the CD3$\zeta$ domain using the NheI and BspEI cloning sites using standard molecular cloning techniques.

293T cells (ATCC CRL-3216) were transiently transfected with third generation lentiviral plasmids to generate viral supernatant. 293T cells were plated in poly-D lysine coated 15 cm tissue culture plates (Corning; Tewksbury, Mass.) in DMEM supplemented with 10% heat inactivated fetal bovine serum (Omega Scientific; Tarzana, Calif.), 100 U/mL penicillin, 100 mg/mL streptomycin, and 2 mM L-glutamine (Invitrogen) and allowed to adhere for 16 hours. The following day, GFP or FLT3 CAR containing plasmids, pMDLg/pRRE and pRSV-Rev packaging, and pMD-G envelope plasmids were lipid transfected into the 293T cells using LIPOFECTAMINE™ 3000 (Invitrogen), as per the manufacturer's protocol. Media containing the transfection mixture was discarded and replaced with fresh media 4-6 hours after the transfection mixture was added. Viral supernatant was collected at 24, 48 and 72 hours post-transfection, centrifuged at 1200 rpm for 6 minutes to remove cells, and stored at −80° C. until use.

Human elutriated lymphocytes from normal donors were used as a source of T cells for experiments. Donor lymphocytes were cleared of red blood cells using Lymphocyte Separation Medium (Lonza; Basel, Switzerland) as per manufacturer's protocol and cryopreserved in heat inactivated fetal bovine serum (FBS; Omega Scientific) with 10% dimethyl sulfoxide (DMSO; Sigma Aldrich; St Louis, Mo.) and stored in liquid nitrogen.

Figure 5:
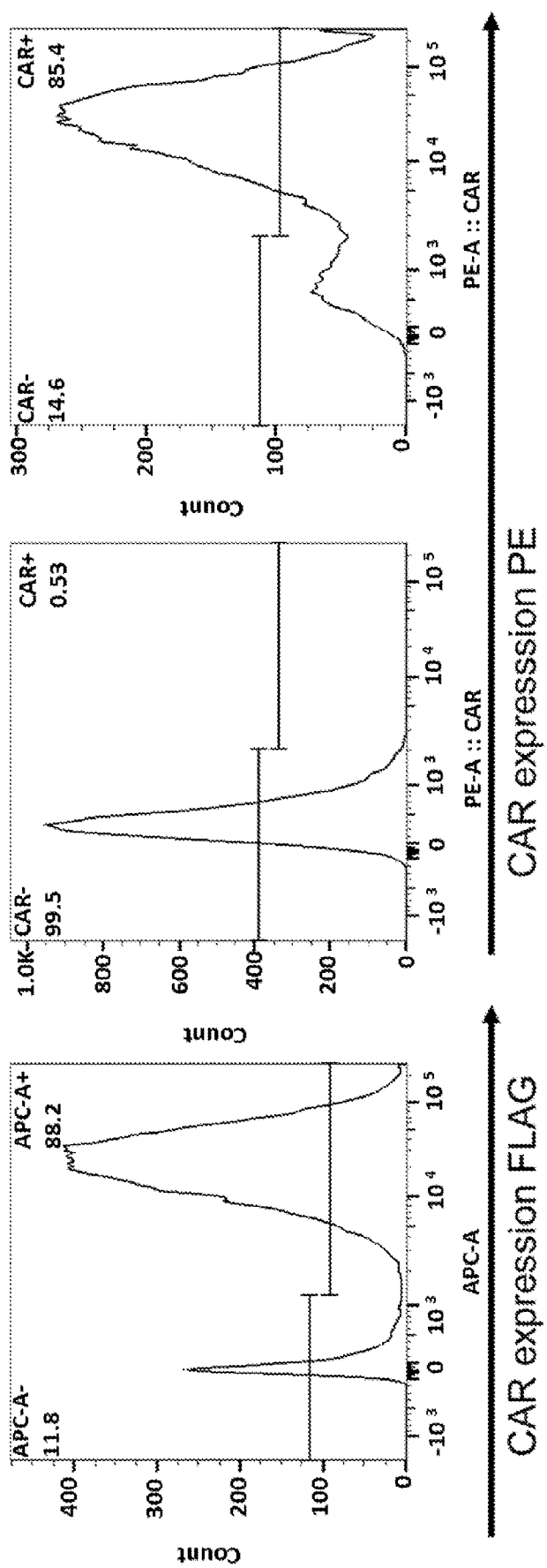
FIG. 5 is a series of flow cytometry plots showing FLT3 CAR T cell transduction. The transduction efficiency of FLT3 CAR transduced T cells was determined on day 9 of T cell culture. FLT3 CAR expression was determined using biotinylated protein L. Detection of FLT3 CAR on transduced T cells was detected by staining with primary conjugated anti-FLAG antibody (left panel 88.2% positive). Detection of FLT3 CAR on transduced T cells was also determined by staining with biotinylated protein L, which is a bacterial protein that binds to a subset of kappa light chains of antibodies, and streptavidin PE (right panel, 85.4% positive). Streptavidin PE only stained FLT3 CAR T cells were used as a negative control (middle panel 0.53%).

Elutriated lymphocytes were thawed and cultured in T cell expansion media (TCEM) which consists of AIM-V media (Invitrogen) supplemented with $\kappa$% heat inactivated FBS (Omega Scientific), 100 U/mL penicillin, 100 mg/mL streptomycin, 15 mM HEPES, and 2 mM L-glutamine (Invitrogen) and 40 IU/ml IL-2 with DYNABEADS™ Human T-Expander CD3/CD28 beads (Invitrogen) at a 3:1 bead to cell ratio. Cells were cultured for 2 days prior to transduction with viral supernatant. Two million T cells were plated per well of a 6-well plate in 1 ml TCEM+3 ml viral supernatant with a final concentration of 40 IU/mL of IL-2 and 10 mg/mL of protamine sulfate. Six-well plates of T cells were centrifuged at 872 g for 2 hours at 32° C. and then incubated at 37° C. overnight. The following day, DYNABEADS™ were removed using a magnetic rack and the T cells were cultured in fresh TCEM with 100 IU/mL IL2 at 500,000 cells/mL. T cells were cultured until day 9 in TCEM with 100 IU/mL of IL-2 maintaining the cells below 1 million/mL and the T cell transduction was determined by flow cytometry (FIG. 5).

Figure 6:
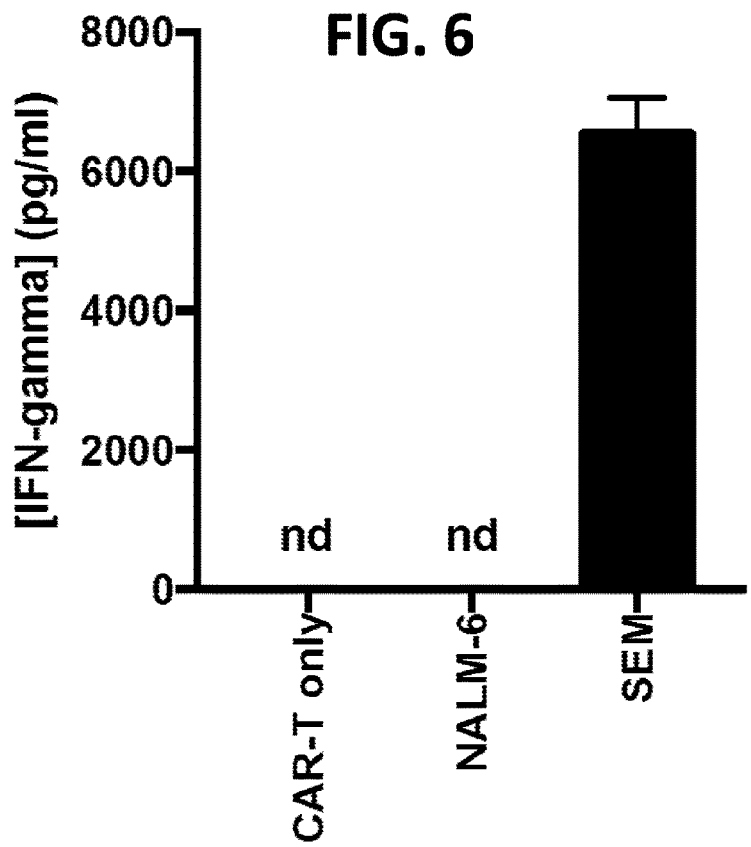
FIG. 6 is a graph showing that T cells expressing FLT3-targeted CARs secrete high levels of IFN-γ when co-cultured with FLT3-expressing ALL cells. FLT3-targeted CAR T cells were co-cultured in 96-well plates with ALL cell lines that express varying levels of FLT3 at an effector to target ratio of 1:1. FLT3 CAR T cells plated alone and NALM-6 cells were used as negative controls. IFN-γ levels were measured from cell culture supernatant.
Figure 7:
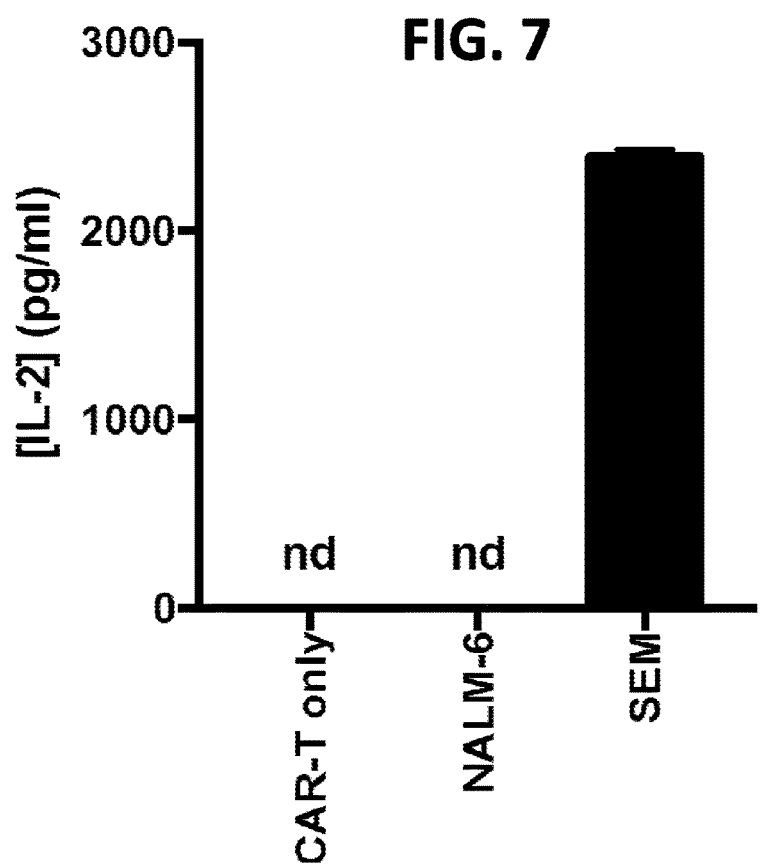
FIG. 7 is a graph showing that T cells expressing FLT3-targeted CARs secrete high levels of IL-2 when co-cultured with FLT3-expressing ALL cells. FLT3-targeted CAR T cells were co-cultured in 96-well plates with ALL cell lines that express varying levels of FLT3 at an effector to target ratio of 1:1. FLT3 CAR T cells plated alone and NALM-6 cells were used as negative controls. IL-2 levels were measured from cell culture supernatant.
Figure 8:
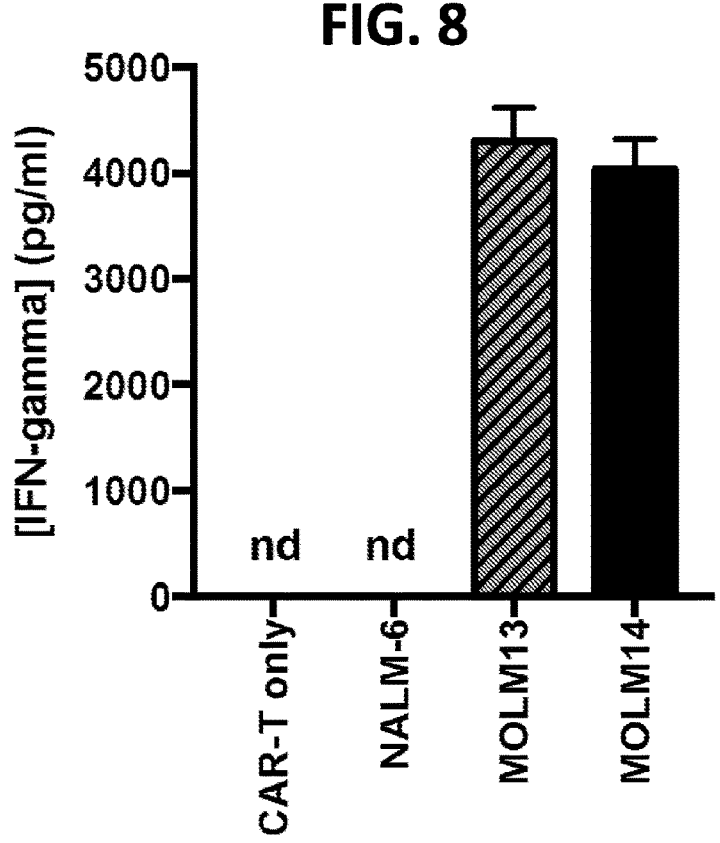
FIG. 8 is a graph showing that T cells expressing FLT3-targeted CARs secrete high levels of IFN-γ when co-cultured with FLT3-expressing AML cells. FLT3-targeted CAR T cells were co-cultured in 96-well plates with AML cell lines that express varying levels of FLT3 at an effector to target ratio of 1:1. FLT3 CAR T cells plated alone and NALM-6 cells were used as negative controls. IFN-γ levels were measured from cell culture supernatant.
Figure 9:
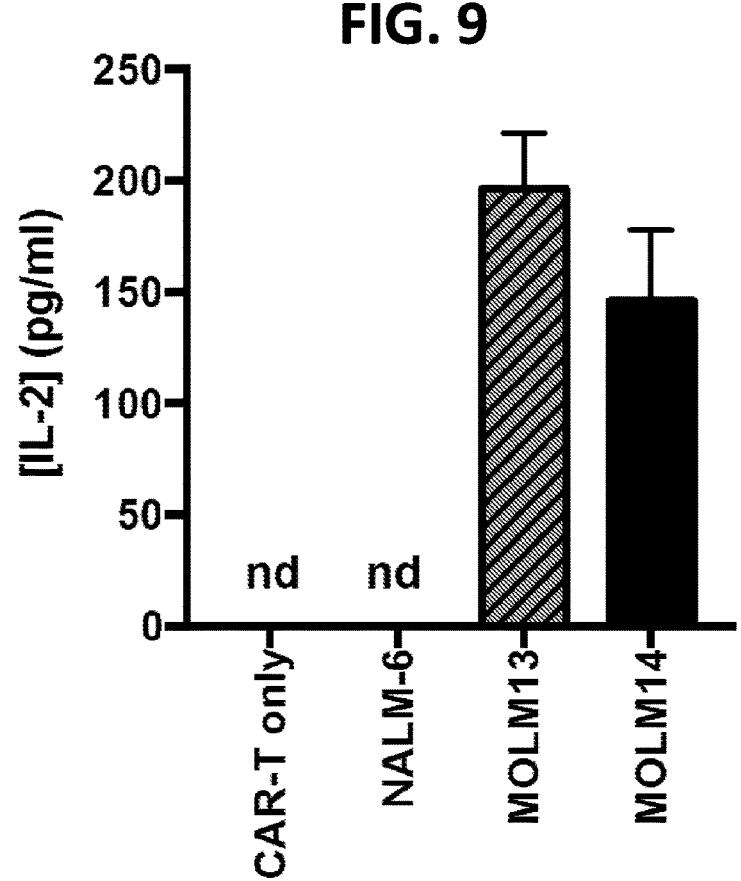
FIG. 9 is a graph showing that T cells expressing FLT3-targeted CARs secrete high levels of IL-2 when co-cultured with FLT3-expressing AML cells. FLT3-targeted CAR T cells were co-cultured in 96-well plates with AML cell lines that express varying levels of FLT3 at an effector to target ratio of 1:1. FLT3 CAR T cells plated alone and NALM-6 cells were used as negative controls. IL-2 levels were measured from the cell culture supernatant.
Figure 10:
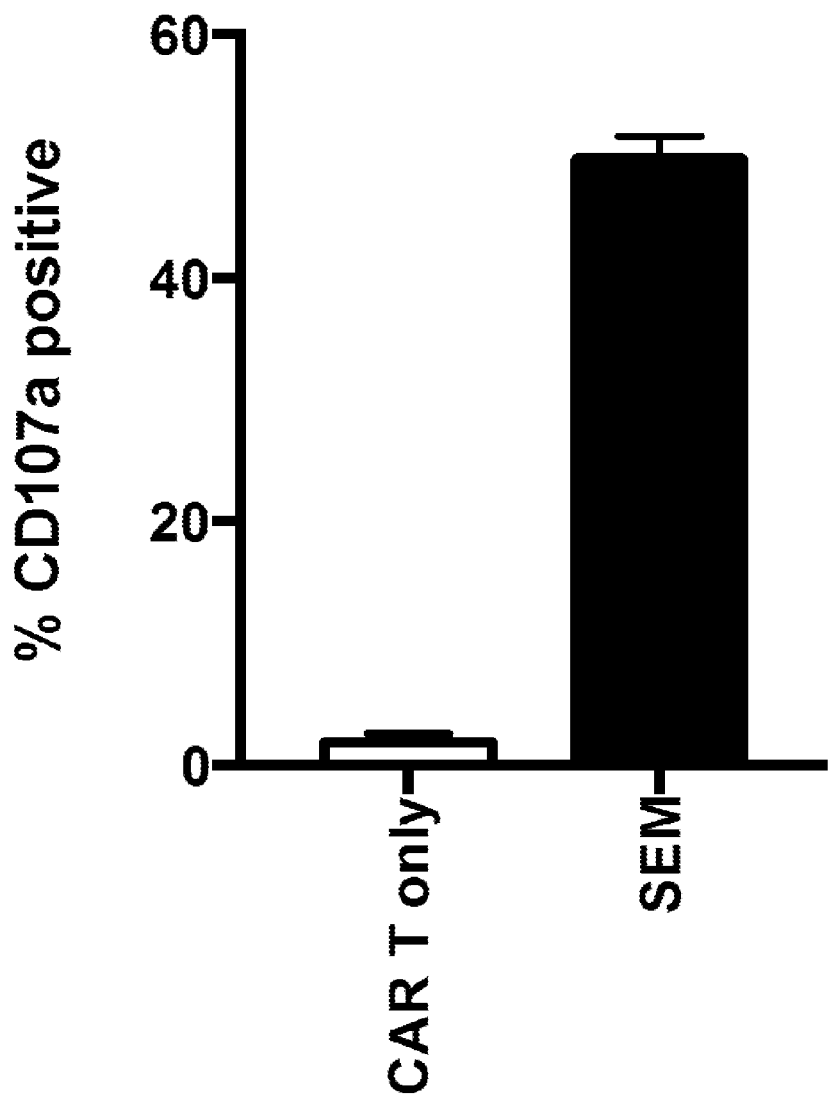
FIG. 10 is a graph showing that T cells expressing FLT3-targeted CARs degranulate when co-cultured with FLT3-expressing ALL cells. FLT3-targeted CAR T cells were co-cultured in 96-well plates with various SEM ALL cells that express FLT3, at an effector to target ratio of 1:2. FLT3 CAR T cells plated alone were used as negative controls. CD107a levels were measured on cells and the percentage of CD107a positive cells was determined by flow cytometry.

FLT3 CAR transduced T cells were co-cultured with various ALL and AML cell lines with varying expression of FLT3 as determined FIG. 3. Acute lymphoblastic NALM6 (DSMZ ACC 128) and SEM (ACC 546) leukemia cell lines, and acute myeloid MOLM13 (DSMZ ACC 554) and MOLM14 (DSMZ ACC 577) leukemia cell lines were used as target tumor cell lines to determine the ability of FLT3 CAR T cells to produce IFN-γ and IL-2 in response to target recognition and activation of the CAR T cells. T cells (100,000/well) and leukemia cells (100,000/well) were co-incubated in 96-well plates for 16 hours in 200 mL/well of RPMI 1640 (Invitrogen; Carlsbad, Calif.) media supplemented with 10% heat inactivated fetal bovine serum (Omega Scientific; Tarzana, Calif.), 100 U/mL penicillin, 100 mg/mL streptomycin, and 2 mM L-glutamine (Invitrogen). The following day, the plates were centrifuged at 1200 rpm for 6 minutes and 150 mL of supernatant was carefully taken for analysis by enzyme linked immunosorbent assay (ELISA). For IFN-γ, the Human IFN-gamma Quantikine ELISA (R&D systems; Minneapolis, Minn.) was used as per manufacturer's protocol and read on a Spectramax MS microplate reader (Molecular Devices; Sunnyvale, Calif.). For IL-2, the Human IL-2 Quantikine ELISA was used according to the manufacturer's protocol (R&D systems; Minneapolis, Minn.) and read on a Spectramax MS microplate reader (Molecular Devices; Sunnyvale, Calif.). Data was then plotted using GraphPad Prism (GraphPad Software; La Jolla, Calif.). As shown in FIG. 6 and FIG. 7, T cells expressing the FLT3-targeted CARs secrete high levels of IFN-γ and IL-2 when co-cultured with FLT3-expressing ALL cells (SEM cells). Similarly, T cells expressing the FLT3-targeted CAR secrete high levels of IFN-γ and IL-2 when co-cultured with FLT3-expressing AML cells (MOLM13 and MOLM14 cells) (FIG. 8 and FIG. 9). As shown in FIG. 10, T cells expressing the FLT3-targeted CAR degranulate when co-cultured with FLT3-expressing ALL cells (SEM cells).

Figure 11:
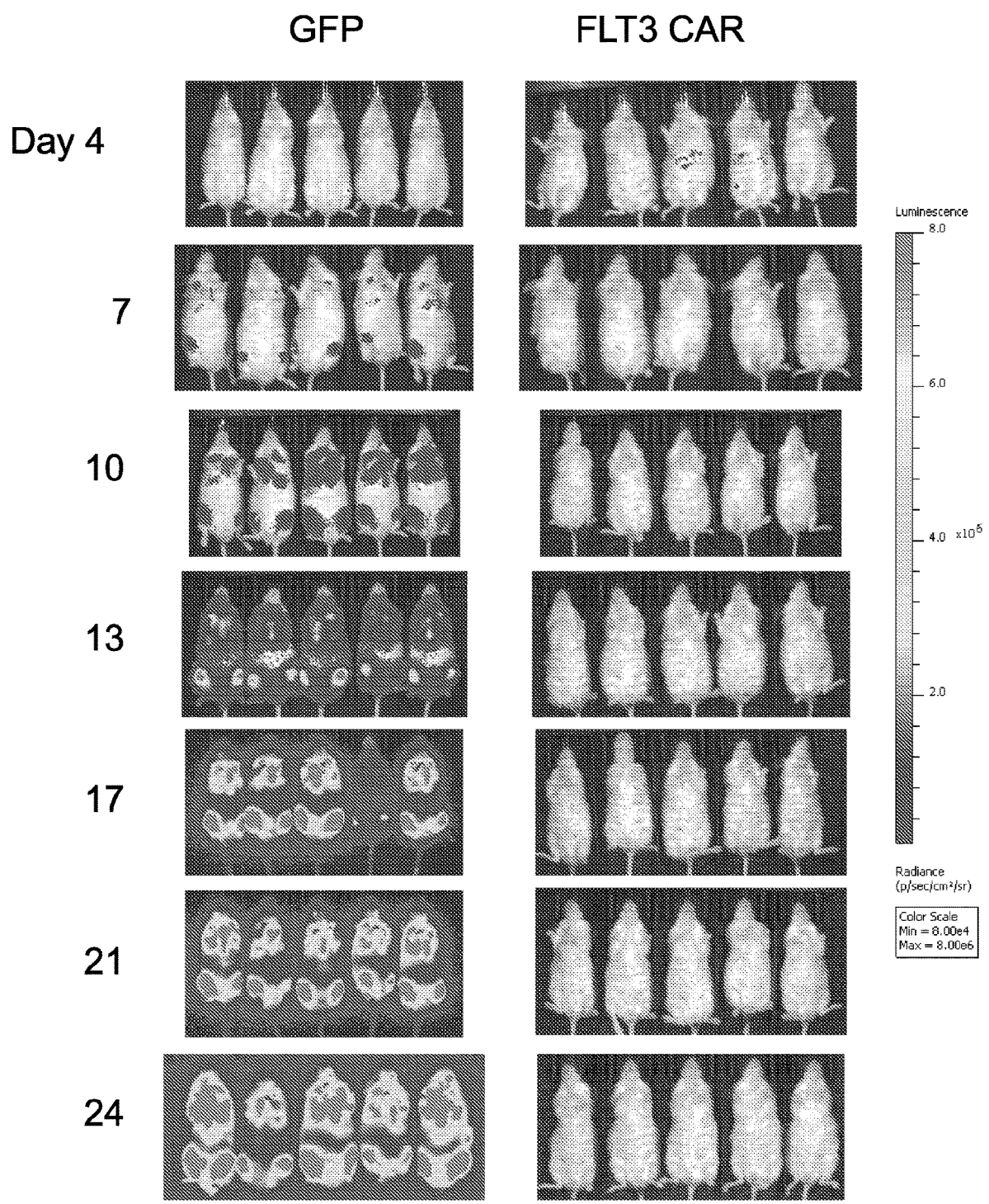
FIG. 11 is a series of bioluminescence images showing that T cells expressing FLT3-targeted CARs are able to eradicate FLT3-expressing ALL in vivo. SEM ALL cells were injected intravenously (IV) into NSG mice and monitored for leukemia progression by bioluminescence imaging. NSG mice with leukemia were imaged 4 minutes after intraperitoneal (IP) injection with 3 mg D-luciferin for 1 minute. GFP or FLT3 CAR transduced T cells were injected on day 4 when a detectable amount of leukemia was observed and the leukemia progression or regression was measured.
Figure 12:
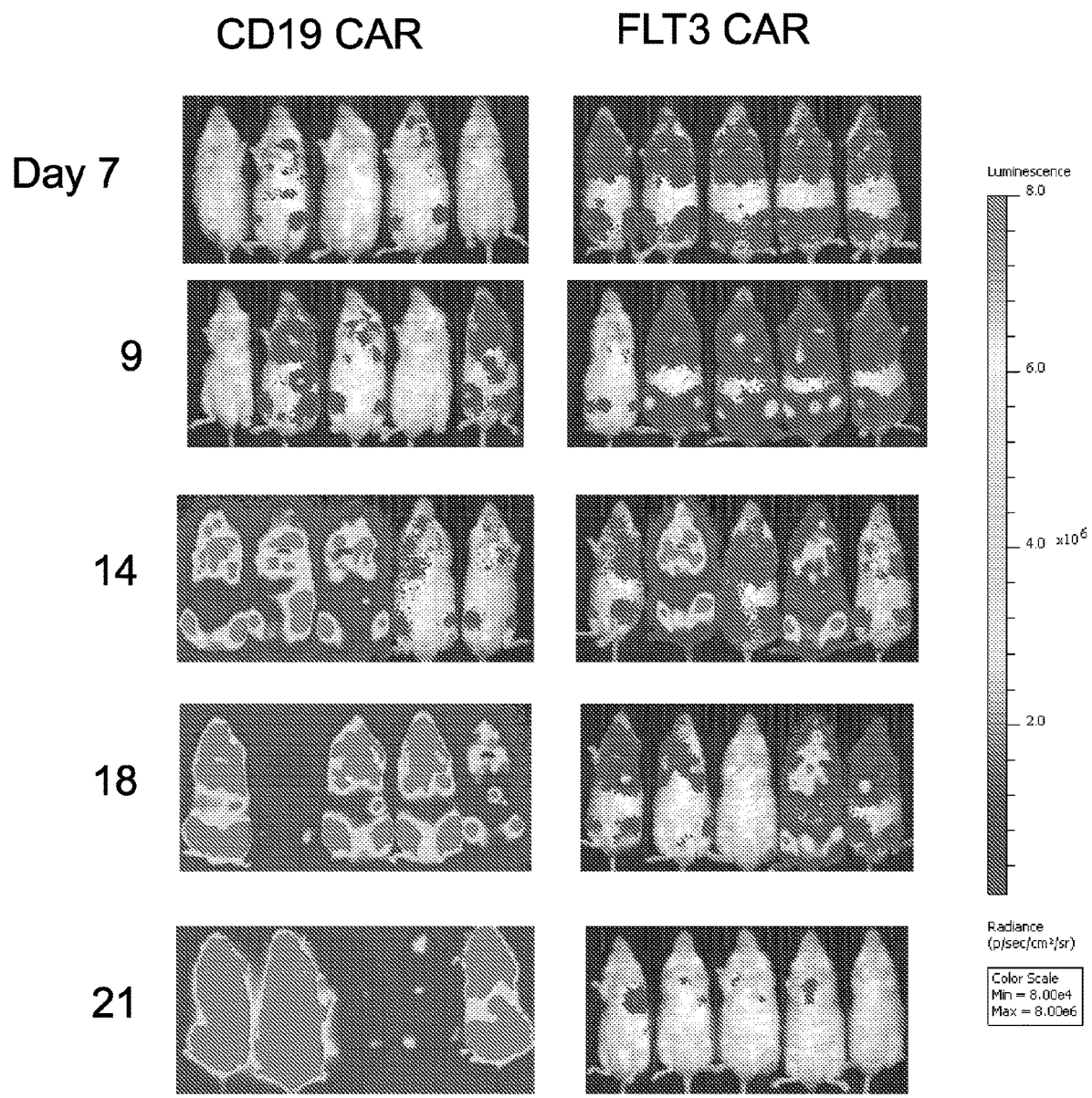
FIG. 12 is a series of bioluminescence images showing that T cells expressing FLT3-targeted CARs are able to eradicate FLT3-expressing AML in vivo. MOLM14 AML cells were injected intravenously (IV) into NSG mice and monitored for leukemia progression by bioluminescence imaging. NSG mice with leukemia were imaged 4 minutes after intraperitoneal (IP) injection with 3 mg D-luciferin for 1 minute. CD19 or FLT3 CAR transduced T cells were injected on day 10 when a detectable amount of leukemia was observed and the leukemia progression or regression was measured.

Further studies of the FLT3-targeted CAR were performed in animals. One million luciferase positive ALL or AML cell lines were intravenously (IV) injected into NSG mice (NOD scid gamma, NOD.Cg-Prkdc$^{scid}$ Il2rg$^{tm1Wjl}$/SzJ) (The Jackson Laboratory; Bar Harbor, Me.) and monitored for leukemia progression by bioluminescence using a Xenogen IVIS Lumina imaging system (Caliper Life Sciences; Hopkinton, Mass.). NSG mice with leukemia were imaged 4 minutes after intraperitoneal (IP) injection with 3 mg D-luciferin (Caliper Life Sciences) for 1 minute. Living Image software (Caliper Life Sciences) was used to analyze the bioluminescent signal from animals with leukemia as photons/s/cm$^2$/sr. GFP or FLT3 CAR transduced T cells were injected on the same day when a detectable amount of leukemia was observed and the leukemia progression or regression was measured twice a week. As shown in FIG. 11, T cells expressing FLT3-targeted CARs are able to eradicate FLT3-expressing ALL in vivo. Similarly, T cells expressing FLT3-targeted CARs are able to eradicate FLT3-expressing AML in vivo (FIG. 12).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody that binds Fms-like tyrosine kinase 3 (FLT3), or an antigen-binding fragment thereof, comprising:
a variable heavy (VH) domain and a variable light (VL) domain, wherein the VH domain of the antibody comprises the complementarity determining region (CDR) sequences of SEQ ID NO: 1 and the VL domain of the antibody comprises the CDR sequences of SEQ ID NO: 2.

2. The monoclonal antibody or antigen-binding fragment of claim 1, wherein the CDR sequences are determined using the IMGT, Kabat or Chothia numbering scheme.

3. The monoclonal antibody or antigen-binding fragment of claim 1, wherein:
the VH domain comprises residues 26-33, 51-58 and 97-105 of SEQ ID NO: 1 and the VL domain comprises residues 27-37, 55-57 and 94-102 of SEQ ID NO 2.

4. The monoclonal antibody or antigen-binding fragment of claim 1, wherein:
the amino acid sequence of the VH domain comprises SEQ ID NO: 1 and the amino acid sequence of the VL domain comprises SEQ ID NO: 2.

5. The antigen-binding fragment of claim 1, wherein the antigen-binding fragment is an Fab fragment, an Fab' fragment, an F(ab)'$_2$ fragment, a single chain variable fragment (scFv) or a disulfide stabilized variable fragment (dsFv).

6. The monoclonal antibody of claim 1, wherein the antibody is an IgG.

7. The monoclonal antibody or antigen-binding fragment of claim 1, which is a fully human, chimeric or synthetic antibody or antigen-binding fragment.

8. A chimeric antigen receptor (CAR) comprising the monoclonal antibody or antigen-binding fragment of claim 1.

9. The CAR of claim 8, further comprising a hinge region, a transmembrane domain, a costimulatory signaling moiety, a signaling domain, or any combination thereof.

10. The CAR of claim 9, wherein:
the hinge region comprises a CD8α hinge region;
the transmembrane domain comprises a CD8α transmembrane domain;
the costimulatory signaling moiety comprises a 4-1BB signaling moiety; and/or
the signaling domain comprises a CD3ζ signaling domain.

11. The CAR of claim 8, comprising the amino acid sequence of SEQ ID NO: 19.

12. An immunoconjugate comprising the monoclonal antibody or antigen-binding fragment of claim 1 and an effector molecule.

13. The immunoconjugate of claim 12, wherein the effector molecule is a toxin or a detectable label.

14. An antibody-drug conjugate (ADC) comprising a drug conjugated to the monoclonal antibody or antigen-binding fragment of claim 1.

15. A multi-specific antibody comprising the monoclonal antibody or antigen-binding fragment of claim 1 and at least one additional monoclonal antibody or antigen-binding fragment thereof.

16. The multi-specific antibody of claim 15, which is a bispecific antibody or a trispecific antibody.

17. An antibody-nanoparticle conjugate, comprising a nanoparticle conjugated to the monoclonal antibody or antigen-binding fragment of claim 1.

18. A fusion protein comprising the monoclonal antibody or antigen-binding fragment of claim 1 and a heterologous protein or peptide.

19. The fusion protein of claim 18, wherein the heterologous protein is an Fc protein.

20. A composition comprising a pharmaceutically acceptable carrier and the monoclonal antibody or antigen-binding fragment of claim 1.

21. A method of treating an FLT3-associated cancer in a subject, comprising administering to the subject the monoclonal antibody or antigen-binding fragment of claim 1.

22. The method of claim 21, wherein the FLT3-associated cancer is a leukemia.

23. The method of claim 22, wherein the leukemia is acute lymphoblastic leukemia (ALL) or acute myeloid leukemia (AML).

24. A method of inhibiting metastasis of an FLT3-positive cancer in a subject, comprising administering to the subject the monoclonal antibody or antigen-binding fragment of claim 1.

25. A method of detecting expression of FLT3 in a sample, comprising:
contacting the sample with the monoclonal antibody or antigen-binding fragment of claim 1; and
detecting binding of the antibody to the sample, thereby detecting expression of FLT3 in the sample.

26. The method of claim 25, wherein the sample is obtained from a subject suspected of having an FLT3-associated cancer.

* * * * *